US009002072B2

(12) United States Patent
Tarnowski et al.

(10) Patent No.: US 9,002,072 B2
(45) Date of Patent: Apr. 7, 2015

(54) SYSTEM FOR DETECTION OF NON-UNIFORMITIES IN WEB-BASED MATERIALS

(75) Inventors: Catherine P. Tarnowski, Mahtomedi, MN (US); Kenneth G. Brittain, Cottage Grove, MN (US); David L. Hofeldt, Oakdale, MN (US); Andrzej P. Jaworski, Woodbury, MN (US); Gregory D. Kostuch, Mahtomedi, MN (US); John A. Ramthun, Hudson, WI (US); Evan J. Ribnick, St. Louis Park, MN (US); Esa H. Vilkama, Plymouth, MN (US); Derek H. Justice, Cary, NC (US); Guillermo Sapiro, Durham, NC (US)

(73) Assignee: 3M Innovative Properties Company, St. Paul, MN (US)

( * ) Notice: Subject to any disclaimer, the term of this patent is extended or adjusted under 35 U.S.C. 154(b) by 38 days.

(21) Appl. No.: 13/984,764

(22) PCT Filed: Feb. 14, 2012

(86) PCT No.: PCT/US2012/024987
§ 371 (c)(1),
(2), (4) Date: Aug. 9, 2013

(87) PCT Pub. No.: WO2012/115819
PCT Pub. Date: Aug. 30, 2012

(65) Prior Publication Data
US 2013/0322733 A1 Dec. 5, 2013

Related U.S. Application Data

(60) Provisional application No. 61/446,404, filed on Feb. 24, 2011.

(51) Int. Cl.
*G06K 9/00* (2006.01)
*G06T 7/00* (2006.01)
(Continued)

(52) U.S. Cl.
CPC ............ *G06T 7/0004* (2013.01); *G06K 9/6253* (2013.01); *G06K 9/6218* (2013.01);
(Continued)

(58) Field of Classification Search
USPC ......... 382/100, 108, 111, 112, 141, 155–160; 348/86, 88, 92, 125–135; 700/95–212; 250/559.01–559.08
See application file for complete search history.

(56) References Cited

U.S. PATENT DOCUMENTS 4,728,800 A * 3/1988 Surka ........................ 250/559.42
5,308,010 A * 5/1994 Hakiel .......................... 242/534
(Continued)

FOREIGN PATENT DOCUMENTS

JP 2010-054346 3/2010
KR 10-2001-0101697 11/2001
WO WO 2010/059679 5/2010

OTHER PUBLICATIONS

Andoni, A. et al.; "Near-Optimal Hashing Algorithms for Approximate Nearest Neighbor in High Dimensions"; Communications of the ACM; vol. 51, No. 1; 2008; pp. 117-122.

(Continued)

Primary Examiner — Anand Bhatnagar
(74) Attorney, Agent, or Firm — James A. Baker

(57) ABSTRACT

A system is described for detecting the presence of non-uniformity patterns and providing output indicative of a severity of each type of non-uniformity pattern. The system includes a computerized rating tool that assists a user in efficiently and consistently assigning expert ratings (i.e., labels) to a large collection of training images representing samples of a given product. In addition, the rating software develops a model that allows a computerized inspection system to detect the presence of non-uniformity patterns in a manufactured web material in real time and provide output indicative of a severity level of each pattern on a continuous scale. The system also includes algorithmic and hardware approaches to significantly that increase the throughput of the inspection system.

18 Claims, 19 Drawing Sheets

(51) Int. Cl.
G06K 9/62 (2006.01)
G06Q 10/06 (2012.01)
G01N 21/89 (2006.01)

(52) U.S. Cl.
CPC .............. *G06Q 10/06* (2013.01); *G01N 21/89* (2013.01); *G06K 2209/19* (2013.01); *G06T 2207/20081* (2013.01); *G06T 2207/30124* (2013.01)

(56) References Cited

U.S. PATENT DOCUMENTS

| | | | | |
|---|---|---|---|---|
| 5,893,055 | A * | 4/1999 | Chen | 702/189 |
| 5,999,636 | A * | 12/1999 | Juang | 382/112 |
| 6,411,860 | B1 * | 6/2002 | Chen | 700/129 |
| 6,778,694 | B1 * | 8/2004 | Alexandre | 382/141 |
| 6,870,965 | B2 | 3/2005 | Kim et al. | |
| 6,999,614 | B1 | 2/2006 | Bakker et al. | |
| 7,295,700 | B2 | 11/2007 | Schiller et al. | |
| 7,359,544 | B2 | 4/2008 | Gao et al. | |
| 7,545,985 | B2 * | 6/2009 | Zhang et al. | 382/224 |
| 2002/0009220 | A1 | 1/2002 | Tanaka | |
| 2002/0110269 | A1 * | 8/2002 | Floeder et al. | 382/141 |
| 2011/0188735 | A1 | 8/2011 | Hosoya et al. | |

OTHER PUBLICATIONS

Clausi, D. et al.; "Designing Gabor filters for optimal texture separability"; Pattern Recognition; vol. 33, No. 11; 2000; pp. 1835-1849.
Daugman, J.; "Uncertainty relation for resolution in space, spatial frequency, and orientation optimized by two-dimensional visual cortical filters"; Journal of the Optical Society of America A; vol. 2, No. 7; 1985; pp. 1160-1169.
Day, W. et al.; "Efficient Algorithms for Agglomerative Hierarchical Clustering Methods"; Journal of Classification; vol. 1, No. 1; 1984; pp. 7-24.
Greenspan, H. et al.; "Rotation Invariant Texture Recognition Using a Steerable Pyramid"; Proc. 12th Int'l Conf. Pattern Recognition; vol. 2; 1994; pp. 162-167.
Haley, G.; "Rotation-Invariant Texture Classification Using Modified Gabor Filters"; Proc. Second IEEE Int'l Conf. Image Processing; vol. 1; 1995; pp. 262-265.
Jain, A. et al.; "Unsupervised Texture Segmentation Using Gabor Filters"; Pattern Recognition; vol. 24, No. 12; 1991; pp. 1167-1186.
Lafon, S. et al.; "Diffusion Maps and Coarse-Graining: A Unified Framework for Dimensionality Reduction, Graph Partitioning, and Data Set Parameterization"; IEEE Transactions on Pattern Analysis and Machine Intelligence; vol. 28, No. 9; 2006; pp. 1393-1403.
Malik, J. et al.; "Preattentive texture discrimination with early vision mechanisms"; J. Optical Soc. Am. A.; vol. 7, No. 5; 1990; pp. 923-932.
Moore, A.; "The Anchors Hierarchy: Using the Triangle Inequality to Survive High Dimensional Data"; Proceedings of the 12th Conference on Uncertainty in Artificial Intelligence; 2000; pp. 397-405.
Rigopoulos, A. et al.; "Principal Components Analysis in Estimation and Control of Paper Machines"; Computers Chem. Engng. vol. 20; 1996; pp. S1059-S1064.
Rigopoulos, A. et al.; "Identification of Full Profile Disturbance Models for Sheet forming Processes"; AIChE Journal; vol. 43, No. 3; 1997; pp. 727-739.
Seung, H. et al.; "Perspectives: Cognition: The Manifold Ways of Perception"; Science; vol. 290, No. 5500; pp. 2268-2269.
Tuzel, O. et al.; "Region Covariance: A Fast Descriptor for Detection and Classification"; Proceedings of the European Conference on Computer Vision; 2006; 12 pgs.
Zhu, X. et al.; "Learning from Labeled and Unlabeled Data with Label Propagation"CMU CALD Technical Report CMU-CALD-02-107; Jun. 2002; 19 pgs.

* cited by examiner

SYSTEM FOR DETECTION OF NON-UNIFORMITIES IN WEB-BASED MATERIALS

CROSS REFERENCE TO RELATED APPLICATION

This application claims the benefit of U.S. Provisional Patent Application No. 61/446,404, filed Feb. 24, 2011, the disclosure of which is incorporated by reference herein in its entirety.

TECHNICAL FIELD

The invention relates to automated inspection systems, such as computerized systems for inspection of moving webs.

BACKGROUND

Computerized inspection systems for the analysis of moving web materials have proven critical to modern manufacturing operations. The goal of a production line is to produce material which is perfectly uniform and devoid of variability. However, non-uniformity is a common problem when manufacturing web-based materials. This can be caused by any number of process variables or formulation errors. Consequently, it is becoming increasingly common to deploy imaging-based inspection systems that can automatically classify the quality of a manufactured product based on digital images captured by optical inspection sensors (e.g., cameras). Some inspection systems apply algorithms, which are often referred to as "classifiers," that attempt to assign a rating to each captured digital image (i.e., "sample") indicating whether the sample, or portions thereof, is acceptable or unacceptable, in the simplest case.

These inspection systems often attempt to identify "point" defects in which each defect is localized to a single area of the manufactured material. However, other types of defects, referred to "non-uniformity" defects or "patterns" may exist in which the web material exhibits non-uniform variability over a large area. Examples of such non-uniformities include mottle, chatter, banding, and streaks. Non-uniformity-type defects such as these are by definition distributed and non-localized. As a result, such defects may be more difficult for computerized inspection systems to detect and quantify than localized, point defects.

When attempting to detect non-uniformity defects in manufactured material, the inspection system typically collects and processes sample images to extract features indicative of particular non-uniformities. On the basis of these features, the inspection system applies one or more classifiers to produce an assessment of the severity of the non-uniformity. The feature extraction can be computationally intensive and a limiting factor of the inspection process. For example, in this step, high resolution images containing several million pixels are reduced to perhaps no more than fifty representative numbers (or features) through routines that may involve filtering, morphological, temporal, spectral, or statistical processing. The resulting numbers then form the basis for assessing the quality of the underlying product. The amount of time required to collapse millions of pixel values into tens of informative numbers can be substantial and, as such, cannot be performed in real-time for fast production rates, even on modern computers. One possibility could be to purchase higher quantities of more expensive computers, but this solution may make the cost of the inspection systems prohibitively expensive and gives rise to additional implementation problems of data distribution and result aggregation.

SUMMARY

In general, this disclosure describes an overall computerized system to address non-uniformities in manufactured material. For example, the system includes a computerized rating tool that can assist a user in efficiently and consistently assigning expert ratings (i.e., labels) to a large collection of digital images representing samples of a given product. In addition, the rating software may develop a model that allows a computerized inspection system to detect the presence of non-uniformity defects in a manufactured web material in real time and provide output indicative of a severity level of each defect on a continuous scale. That is, the computerized inspection system utilizing the expert ratings as training data to be applied in real-time for detecting the presence of non-uniformity defects, i.e., patterns, and providing output indicative of a severity of each defect. The techniques may provide real-time output that provides a continuous charting of the non-uniformity severity. In other words, rather than being constrained to discrete rating labels, such as "acceptable" of "unacceptable," or a "1", "3", or "5", the computerized inspection system may provide a more continuous ranking of the samples. In addition, techniques are described that increase the throughput of the inspection system that is designed to detect and classify specific patterns in a web-manufactured material. Algorithmic and hardware approaches are described to significantly decrease the average amount of time required to inspect a given quantity of material that is expected to be mostly uniform. The algorithmic techniques described herein involve dynamic (i.e., online) determination of which image features to compute by starting with a base feature set and only triggering additional feature computations as needed. In some embodiments, the computations are performed in graphics processing units (GPUs), which can be optimized for many image processing routines. As such, the techniques may lead to substantial productivity gains.

In one embodiment, a method comprises executing rating software on a computer to automatically assign a discrete rating label for a non-uniform defect to each of a plurality of training images and compute a classification model based on the rating labels assigned to the training samples. The rating software receives input from a user for only a subset of the training images and computes the rating labels for all of the remaining training images based upon the input. The method further comprises processing in real-time a sample image captured from a manufactured web material with hardware components of a pipelined graphical processing unit (GPU) integrated within a computerized inspection system to extract a first plurality of features from the image in parallel; and computing a severity level for the non-uniformity defect for the sample image of the web material with the computerized inspection system from the first plurality of features in accordance with the classification model.

In another embodiment, an online computerized inspection system is described for inspecting web material in real-time and computing a severity of a non-uniformity defect as the web material is manufactured. The inspection system comprises a memory to store a decision-making model that defines a chain of dynamic triggers for selecting in real-time which features to extract from an image, and a computer executing software to process a sample image captured from a manufactured web material currently being manufactured to extract a first set of features. The software applies the model to dynamically trigger selection of additional sets of features to extract from the sample image and invokes hardware components of a pipelined graphical processing unit (GPU) of the inspection system to extract the additional sets of features until the extracted features are sufficient to compute a severity level of a non-uniformity defect for the web material within a defined level of confidence. The dynamic triggering and computations are repeated as necessary as new material is presented to the inspection system.

In another embodiment, an online computerized inspection system is described for inspecting web material in real-time. The inspection system comprises a memory to store a model that represents a continuous ranking of the training images as a plurality of points within a multidimensional feature space, wherein each of the points within the multidimensional space corresponds to a feature vector for a different one of the training images. The inspection system further comprises a pipelined graphical processing unit (GPU) of the inspection system to process a sample image captured from a manufactured web material to extract a plurality of features in parallel from the sample image using parallel hardware components of the GPU. The computerized inspection system computes a severity level of a non-uniform defect from the extracted features for the sample image of the web material on a continuous scale based on the model of the training images.

The techniques described herein have applicability and usefulness in numerous product lines, including any material that is produced on a web. The techniques have broad applicability to a wide range of products in which uniformity is important. A few examples are optical films, window films, and abrasives.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
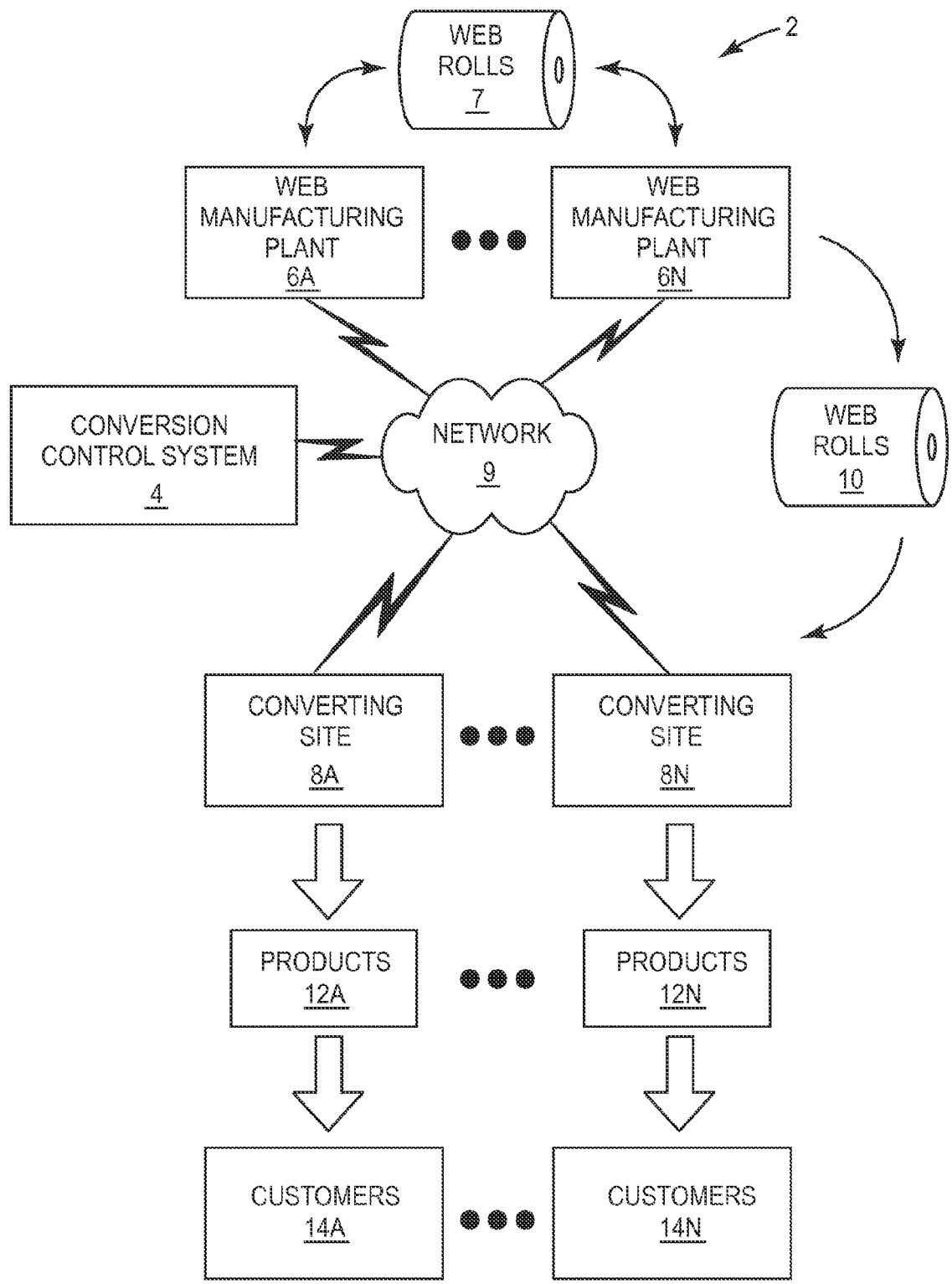
FIG. 1 is a block diagram illustrating an example web manufacturing and conversion system in which the techniques described herein may be applied.

FIG. 1 is a block diagram illustrating an example system 2 in which the techniques described herein may be applied. Web manufacturing plants 6A-6N (web manufacturing plants 6) represent manufacturing sites that produce and ship web material in the form of web rolls 7. Web manufacturing plants 6 may be geographically distributed, and each of the web manufacturing plants may include one or more manufacturing process lines. In general, web rolls 7 may be manufactured by any of manufacturing plants 6 and shipped between the web manufacturing plants for additional processing. Finished web rolls 10 are shipped to converting sites 8A-8N (converting sites 8) for conversion into products 12A-12N (products 12). As shown in FIG. 1, conversion control system 4, web manufacturing plants 6A-6N (web manufacturing plants 6) and converting sites 8A-8N (converting sites 8) are interconnected by a computer network 9 for exchanging information (e.g., defect information) related to manufacture of the web material and conversion into products 12.

In general, web rolls 7, 10 may contain manufactured web material that may be any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

Converting sites 8 may receive finished web rolls 10 from web manufacturing plants 6 and convert finished web rolls 10 into individual sheets for incorporation into products 12 for sale to customers 14A-14N (customers 14). Converting systems may determine into which products 14 a given finished web roll 10 is converted based on a variety of criteria, such as grade levels associated with the product. That is, the selection process of which sheets should be incorporated into which products 12 may be based on the specific grade levels each sheet satisfies. In accordance with the techniques described herein, converting sites 8 may also receive data regarding anomalies, i.e. potential defects, in the finished web rolls 10. Ultimately, converting sites 8 may convert finished web rolls 10 into individual sheets which may be incorporated into products 12 for sale to customers 14A-14N (customers 14).

In order to produce a finished web roll 10 that is ready for conversion into individual sheets for incorporation into products 12, unfinished web rolls 7 may need to undergo processing from multiple process lines either within one web manufacturing plant, for instance, web manufacturing plant 6A, or within multiple manufacturing plants. For each process, a web roll is typically used as a source roll from which the web is fed into the manufacturing process. After each process, the web is typically collected again into a web roll 7 and moved to a different product line or shipped to a different manufacturing plant, where it is then unrolled, processed, and again collected into a roll. This process is repeated until ultimately a finished web roll 10 is produced. For many applications, the web materials for each of web rolls 7 may have numerous coatings applied at one or more production lines of one or more web manufacturing plants 6. The coating is generally applied to an exposed surface of either a base web material, in the case of the first manufacturing process, or a previously applied coating in the case of a subsequent manufacturing process. Examples of coatings include adhesives, hardcoats, low adhesion backside coatings, metalized coatings, neutral density coatings, electrically conductive or nonconductive coatings, or combinations thereof.

Figure 2:
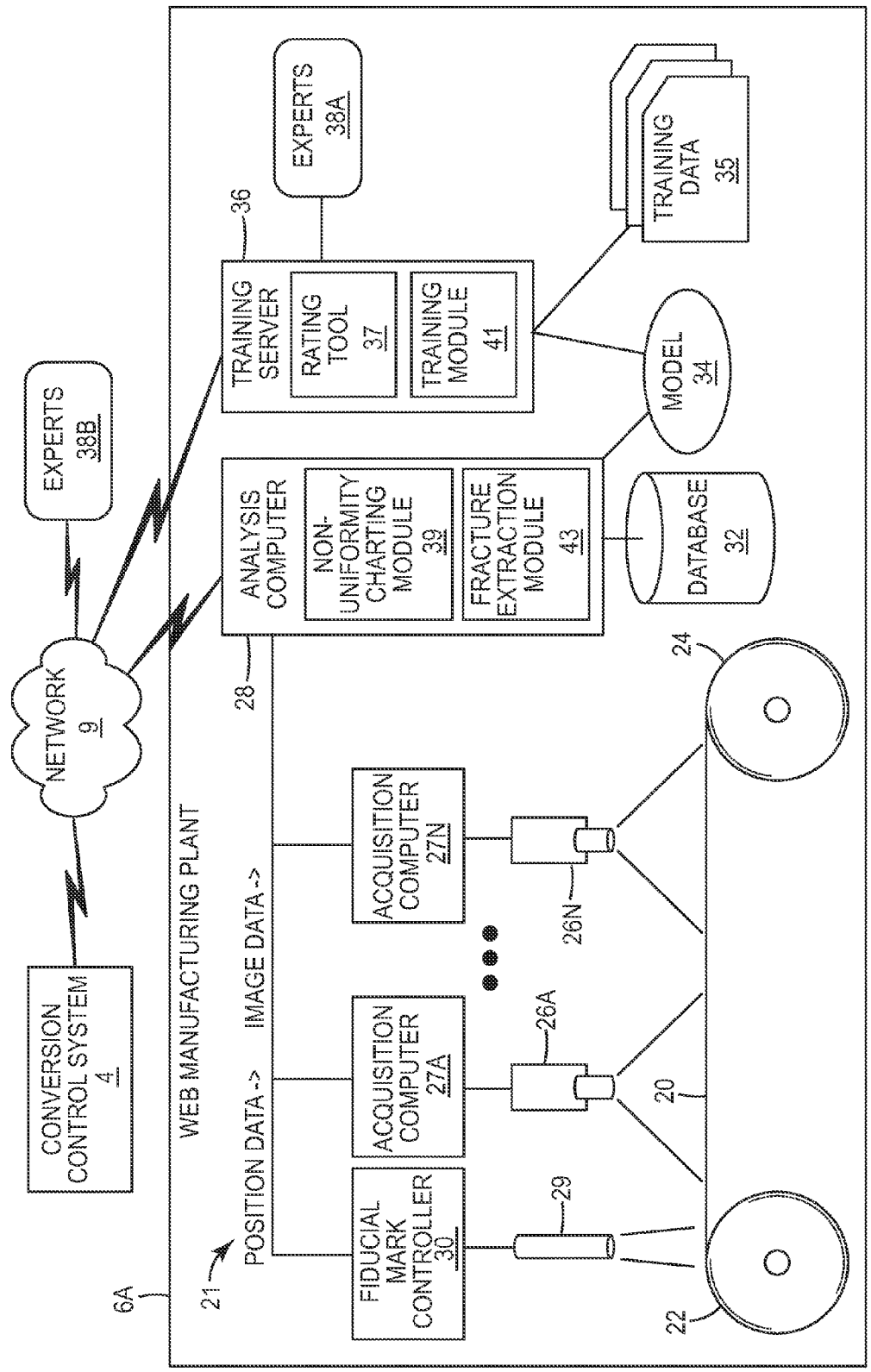
FIG. 2 is a block diagram illustrating an exemplary embodiment of an inspection system in an exemplary web manufacturing plant.

During each manufacturing process for a given one of web rolls 7, one or more inspection systems acquire anomaly information for the web. For example, as illustrated in FIG. 2, an inspection system for a production line may include one or more image acquisition devices positioned in close proximity to the continuously moving web as the web is processed, e.g., as one or more coatings are applied to the web. The image acquisition devices scan sequential portions of the continuously moving web to obtain digital images. The inspection systems analyze the images with one or more algorithms to produce so-called "local" anomaly information that may represent an actual "defect" depending upon the ultimate product 12 into which the web is converted. The inspection systems may, for example, produce anomaly information for "point" defects in which each defect is localized to a single area. As another example, the inspections systems may produce anomaly information for "non-uniform" defects or "non-uniformities" in which the web material exhibits non-uniform variability over a large area larger than that of point defects. Examples of such non-uniformities include mottle, chatter, banding, and streaks.

The inspection systems within web manufacturing plants 6 may apply algorithms for detecting the presence of non-uniformity defects and providing output indicative of a severity of each defect in real-time as the web is manufactured. For example, the computerized inspection systems may provide real-time feedback to users, such as process engineers, within web manufacturing plants 6 regarding the presence of non-uniformities and their severity, thereby allowing the users to quickly respond to an emerging non-uniformity by adjusting process conditions to remedy the problem without significantly delaying production or producing large amounts of unusable material. The computerized inspection systems may apply algorithms to compute the severity level by ultimately assigning a rating label for the non-uniformity (e.g., "good" or "bad") or by producing a measurement of non-uniformity severity of a given sample on a continuous scale or more accurately sampled scale, such as 1.63 on a scale from 0 to 10.

During this process, the inspection systems may apply techniques described herein to dynamically (i.e., in real-time during manufacture of a web material) determine which image features to compute. In one example, the inspection systems start by extracting a base feature set, the contents of such set may vary from system to system, and then triggering the computations of additional feature(s) as needed. For each sample image acquired, the techniques build a "best feature set" in real-time by using the results from successively larger feature sets to trigger the computation of additional features as needed. Each inspection system starts with an appropriate baseline feature set, then based on the values of the base feature set, decides which extra features (if any) to compute. Similarly, these additional features can be analyzed to determine which, if any, additional features are needed. The decision at each step of the feature extraction process is referred to herein as a potential trigger event. In one embodiment, the inspection system makes the decision whether to trigger the computation of additional features at each potential trigger event as to optimize the expected gain in classification accuracy under a controlled Markov chain model.

In some embodiments, analysis computers of the inspection systems process the captured digital images by application of a continuous ranking model that has been developed based on training data. The training data is typically processed during a "training phase" of the algorithms that often employs rather coarse discrete rating labels such as "acceptable" or "unacceptable" or a "1", "3", or "5", and the continuous ranking model is developed to best fit the training data. That is, after the training phase and development of the continuous ranking model, application of the continuous ranking model to the training data will label the training data with a high probability of correctness. Once the model has been developed from the training data, the analysis computers apply the model to samples captured from newly manufactured product, potentially in real-time, during the "classification phase" of the processing and provide a continuous charting of non-uniformity severity that is not constrained to discrete rating labels. The computerized inspection systems may thereby provide a continuous ranking of samples. For example, a computerized inspection system may apply algorithms to produce measurements of severity for non-uniformity defects within a web material on a continuous scale, such as 1.63 on a scale from 0 to 10.

In some embodiments, additional analysis of digital images for a given manufactured web may be performed offline by conversion control system 4. Based on the classifications for a given web, conversion control system 4 may select and generate a conversion plan for each web roll 10. The analysis of the digital images and determination of the severity level may be application-specific in that a certain non-uniformity may result in a defect in one product, e.g., product 12A, whereas the anomaly may not cause a defect in a different product, e.g., product 12B. Each conversion plan represents defined instructions for processing a corresponding finished web roll 10 for creating products 12, which may ultimately be sold to customers 14. For example, a web roll 10 may be converted into final products, e.g., sheets of a certain size, for application to displays of notebook computers. As another example, the same web roll 10 may instead be converted into final products for application to displays of cell phones. Conversion control system 4 may identify which product best achieves certain parameters, such as a maximum utilization of the web, in view of the different defect detection algorithms that may be applied to the anomalies.

FIG. 2 is a block diagram illustrating an exemplary embodiment of an inspection system located within a portion of a web process line 21 in exemplary web manufacturing plant 6A of FIG. 1. In the exemplary embodiment, a segment of a web 20 is positioned between two support rolls 22, 24. Image acquisition devices 26A-26N (image acquisition devices 26) are positioned in close proximity to the continuously moving web 20 and scan sequential portions of the continuously moving web 20 to obtain image data. Acquisition computers 27 collect image data from image acquisition devices 26 and transmit the image data to analysis computer 28.

Image acquisition devices 26 may be conventional imaging devices that are capable of reading a sequential portion of the moving web 20 and providing output in the form of a digital data stream. As shown in FIG. 2, imaging devices 26 may be cameras that directly provide digital data streams or an analog cameras with an additional analog to digital converters. Other sensors, such as, for example, laser scanners, may be utilized as the imaging acquisition devices. A sequential portion of the web indicates that the data is acquired by a succession of single lines. Single lines comprise an area of the continuously moving web that maps to a single row of sensor elements or pixels. Examples of devices suitable for acquiring the image include linescan cameras such as Piranha Models from Dalsa (Waterloo, Ontario, Canada), or Model Aviiva SC2 CL from Atmel (San Jose, Calif.). Additional examples include laser scanners from Surface Inspection Systems GmbH (Munich, Germany) in conjunction with an analog to digital converter.

The image data may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

In some embodiments, fiducial mark controller 30 controls fiducial mark reader 29 to collect roll and position information from web 20. For example, fiducial mark controller 30 may include one or more photo-optic sensors for reading bar codes or other indicia from web 20. In addition, fiducial mark controller 30 may receive position signals from one or more high-precision encoders engaged with web 20 and/or rollers 22, 24. Based on the position signals, fiducial mark controller 30 determines position information for each detected fiducial mark. Fiducial mark controller 30 communicates the roll and position information to analysis computer 28 for association with detected anomalies.

Analysis computer 28 processes streams of image data from acquisition computers 27. In accordance with the techniques described herein, a feature extraction module 43 executes on analysis computer 28 and dynamically determines which image features to compute on a per-image basis in real-time during manufacture of web material 20. That is, for each sample image acquired during manufacture, feature extraction module 43 builds a "best feature set" in real-time by using the results from successively larger feature sets to trigger additional feature computations until severity levels can be computed for each type of potential non-uniformity. In one example embodiment, computerized non-uniformity charting module 39 ("charting module 39") processes the extracted features by applying algorithms that utilize continuous ranking model 34 ("model 34") developed based on training data 35 to detect the presence of non-uniformity defects and provide a continuous charting of a severity level of each defect.

Training data 35 typically consists of a large set of representative sample digital images that have been assigned ratings by one or more experts 38. Previously automatically ranked data can be used for training as well. The digital images may, for example, represent samples taken from web 20 or another web previously produced by web process line 21. Training server 36 may provide an operating environment for execution of software that provides a computerized expert rating tool 37 ("rating tool 37") to assist experts 38 in efficiently and consistently assigning ratings (i.e., labels) to the large collection of digital images representing the samples.

Once training data 35 has been established, training module 41 processes the training data to generate continuous ranking model 34 for subsequent use by charting module 39 for real-time analysis of image data received from acquisition computers 27 for web material 20. In this way, new images of regions of web material 20 can be classified in accordance with continuous ranking model 34. Example defects that may be detected include non-uniformities such as mottle, chatter, banding, and streaks, as well as point defects including spots, scratches, and oil drips.

Analysis computer 28 may store the anomaly information for web 20, including roll identifying information for the web 20 and possibly position information for each anomaly, within database 32. For example, analysis computer 28 may utilize position data produced by fiducial mark controller 30 to determine the spatial position or image region of each anomaly within the coordinate system of the process line. That is, based on the position data from fiducial mark controller 30, analysis computer 28 determines the x, y, and possibly z position or range for each anomaly within the coordinate system used by the current process line. For example, a coordinate system may be defined such that the x dimension represents a distance across web 20, a y dimension represents a distance along a length of the web, an the z dimension represents a height of the web, which may be based on the number of coatings, materials or other layers previously applied to the web. Moreover, an origin for the x, y, z coordinate system may be defined at a physical location within the process line, and is typically associated with an initial feed placement of the web 20. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, database 32 is implemented as a relational database provided by SQL Server™ from Microsoft Corporation.

Once the process has ended, analysis computer 28 may transmit the data collected in database 32 to conversion control system 4 via network 9. For example, analysis computer 28 may communicate the roll information as well as the anomaly information and respective sub-images for each anomaly to conversion control system 4 for subsequent, offline, detailed analysis in accordance with continuous ranking model 34. For example, the information may be communicated by way of database synchronization between database 32 and conversion control system 4. In some embodiments, conversion control system 4 may determine those products of products 12 for which each anomaly may cause a defect, rather than analysis computer 28. Once data for the finished web roll 10 has been collected in database 32, the data may be communicated to converting sites 8 and/or used to mark anomalies on the web roll, either directly on the surface of the web with a removable or washable mark, or on a cover sheet that may be applied to the web before or during marking of anomalies on the web.

The components of analysis computer 28 and training server 36 may be implemented, at least in part, as software instructions executed by one or more processors of analysis computer 28, including one or more hardware microprocessors, digital signal processors (DSPs), application specific integrated circuits (ASICs), field programmable gate arrays (FPGAs), or any other equivalent integrated or discrete logic circuitry, as well as any combinations of such components. The software instructions may be stored within in a non-transitory computer readable medium, such as random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. Although shown for purposes of example as positioned within manufacturing plant 6A, analysis computer 28 as well as training server 36 may be located external to the manufacturing plant, e.g., at a central location or at a converting site. For example, analysis computer 28 and training server 36 may operate within conversion control system 4. In another example, the described components execute on a single computing platform and may be integrated into the same software system.

Figure 3:
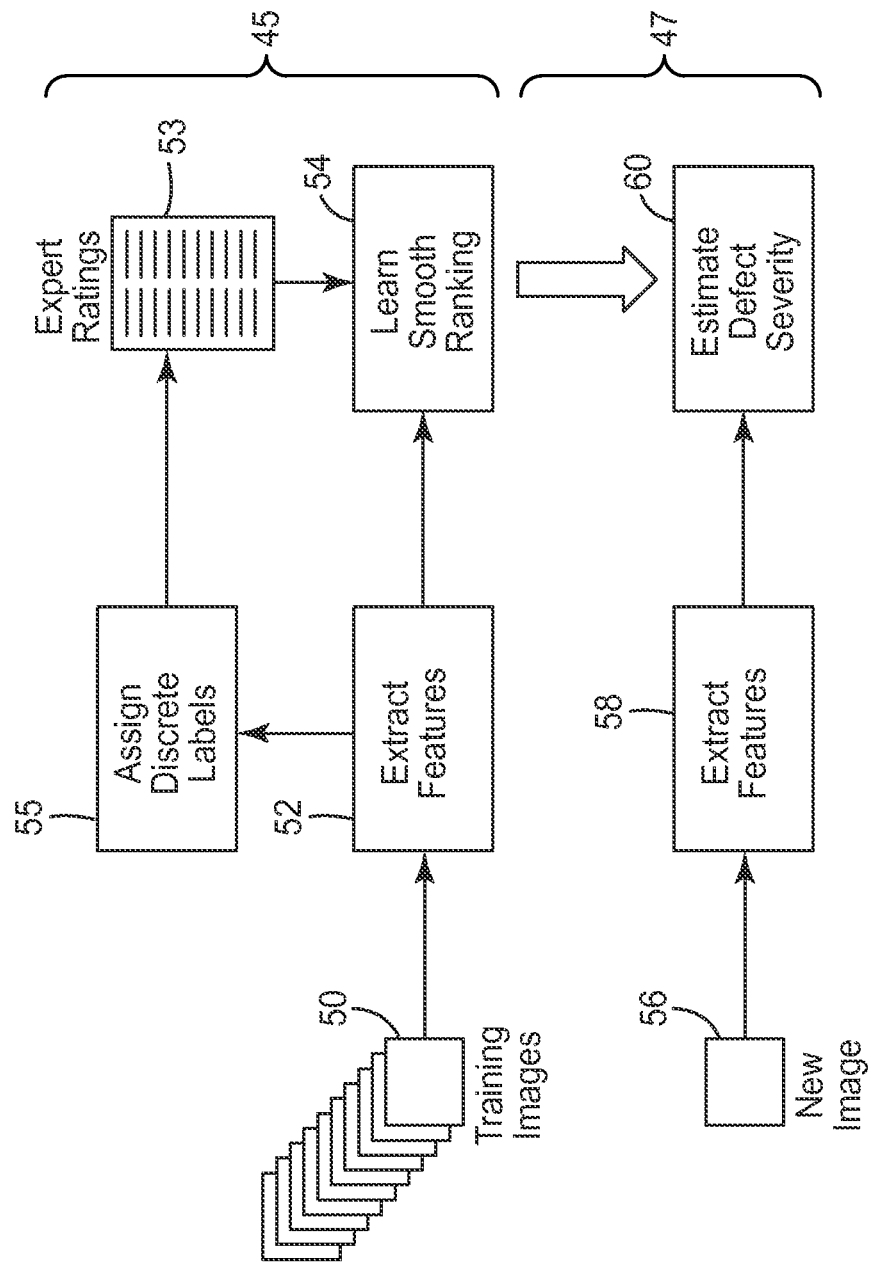
FIG. 3 is a flowchart illustrating an example operation of the systems described herein.

FIG. 3 is a flowchart that provides an overview of the inspection system of FIG. 2. In this example, the process comprises two general phases of processing: training phase 45 and online estimation phase 47.

Initially, training module 41 receives training data 35 as input, typically in the form of a set of images, for which severity rankings are already known on a possibly coarsely discretized scale (50). Next, a feature extraction software module executing on training server 36 processes each of the images to extract features (52). Feature extraction provides a numerical descriptor of each of the images as a compact numerical representation of the relevant information inherent in each image. As feature extraction during the training phase occurs offline, the feature extraction software module may perform the complete set of feature extraction computations for each of the training images. Features can be extracted in any way that preserves useful information about the relationships between images in the training set, and at the same time eliminates un-informative image characteristics. Examples of common feature extraction techniques include convolving the image with a set of filters and computing statistics of the filtered images, or extracting features based on color or intensity histograms. Sometimes the pixel values can be used as features, although in this case there is no compactness in the descriptor, since the entire image must typically be stored. In general, the resulting features are treated as compact descriptions of the relevant information in the corresponding images.

The techniques described herein are not limited to use with any particular feature extraction methodology, and may readily be applied to applications in which other types of features are more appropriate. In general, the features extracted from the images are descriptive in that they contain discriminating information about the images with respect to a particular type of non-uniformity. As such, once features have been extracted, the feature vector corresponding to each image represents most of the relevant information contained in that image.

One exemplary feature extraction algorithm, particularly as it relates to texture, is to compute a small covariance matrix of pixel features across the image or for sub-regions of the image. Once this small covariance matrix (e.g., 5×5) is extracted, pair-wise comparisons between images can be made efficiently based only on these matrices, instead of dealing with the images directly. For example, a grayscale image is defined as a two-dimensional array, indexed by pixel coordinates x and y, as I(x, y). At each pixel location (x, y), a feature vector is extracted based on the intensity values of the pixel and their first and second derivatives at that pixel:

$$f(x, y) = \left( I(x, y) \frac{\partial I(x, y)}{\partial x} \frac{\partial I(x, y)}{\partial y} \frac{\partial^2 I(x, y)}{\partial x^2} \frac{\partial^2 I(x, y)}{\partial y^2} \right)^T. \quad (1)$$

Image derivatives (gradients) can be approximated simply by computing forward or central differences between intensity values at each pixel. Other features, including higher derivatives or results from filtered image(s), can also be incorporated in the vector in (eq. 1). Similarly, not all derivatives need to be included, e.g., if a derivative in a given direction provides no information for the particular defect, it can be removed from (eq. 1). Finally, the covariance matrix of these pixel features is computed across the entire image:

$$C_I = \frac{1}{N-1} \sum_{(x,y) \in I} (f(x, y) - \mu)(f(x, y) - \mu)^T, \quad (2)$$

where N is the number of pixels in the image, and:

$$\mu = \frac{1}{N} \sum_{(x,y) \in I} f(x, y) \quad (3)$$

is the mean of the pixel features. In subsequent processing steps, it may be useful to compute pair-wise distances between images. In the case of these covariance matrix descriptors, pair-wise distances are computed as:

$$d_C(I_1, I_2) = \sqrt{\sum_{i=1}^{3} \ln^2 \lambda_i(C_{I_1}, C_{I_2})}, \quad (4)$$

where $\lambda_i(C_{I1}; C_{I2})$ is the ith generalized eigenvalue of the two covariance matrices. Further details can be found in O. Tuzel, F. Porikli, and P. Meer. "Region Covariance: A Fast Descriptor for Detection and Classification." Proceedings of the European Conference on Computer Vision, 2006, incorporated herein by reference.

After extracting features for each of the training images, experts 38 interact with computerized expert rating tool 37 to assign discrete ratings 53 to each of the digital images in view of the extracted feature vectors in the manner described below (55).

Next, training module 41 process the extracted feature vectors and the expert ratings 53 to generate a continuous ranking of the training images and produce continuous ranking model 34 based on the severity of their non-uniformities (54). Initially, all that is known about each training image is the expert rating, denoting if the corresponding sample is "good" or "bad," or a level "1", "3", or "5" with respect to a particular type of non-uniformity. These expert ratings provide an often coarse ordering of the training images, i.e., the training images can be ranked into 2 or 3 discrete categories, or more categories if the expert is able to provide such finer scale information. Training model 41 uses this coarse ordering as input and learns a continuous ranking in which the training images are ranked from best to worst along a continuous scale with respect to a particular non-uniformity. Although a good ranking should heed the expert ratings as much as possible, for example assigning "good" images lower severity ranking than those labeled "bad," in some instances training module 41 is not completely prevented from violating the coarse ranking implied by the discrete labels, since it is possible, and indeed common, that there are errors in the expert ratings due to the subjective nature of human perception, or even outright mistakes in manual labeling of the training data.

During the online estimation phase 47, charting module 39 applies the learned continuous ranking model 34 in real-time on the production line. As a sample image of the web being produced is captured (56), feature extraction module 43 extracts features from the image (58). As described in further detail below, feature extraction module 43 dynamically determines which image features to compute on a per-image basis in real-time during manufacture of web material 20. For each sample image acquired during manufacture, feature extraction module 43 builds a "best feature set" in real-time by using the results from successively larger feature sets to trigger additional feature computations. Feature extraction module 43 may store a decision-making model (e.g., a Markov model) that defines a chain of dynamic triggers for selecting in real-time which features to extract from the sample image. Feature extraction module 43 applies the model to repeatedly dynamically trigger selection of additional sets of features to extract from the sample image until the extracted features are sufficient to compute a severity level of a non-uniformity defect for the web material (59, 60). As such, the number of features extracted for any given sample image, and the order in which the features are extracted, is dynamically determined in real-time by feature extraction module 43. The computer inspection system may compute the severity level by assigning a severity rating label such as "good" or "bad" or by producing a severity value such as "1.63" on a scale of 1 to 10. The computed severity for the non-uniformity defect may then be output to a user. For example, once the extracted features are sufficient for a severity rating to be assigned based on continuous ranking model 34, the severity rating may be output to the user.

The techniques described herein may be utilizes for training new individuals to become expert raters. That is, the techniques described herein can be used to visually present examples of specific non-uniformity defects, possibly in response to adjustments made by operators to increase or decrease the number and severity of a particular non-uniformity defect. This allows new individual to visualize a defect in the same manner as existing experts and to develop a better understanding of images used to train an expert rating system. For example, the computerized inspection system may process in real-time a sample image captured from a manufactured web material to extract a first plurality of features from the image. Rating tool 37, as implemented as training software for a user, may compute a severity level for the non-uniformity defect for the sample image of the web material with the computerized inspection system from the first plurality of features in accordance with the classification model and then display both the sample image and the severity level computed from the classification model to a user as training information.

Figure 4:
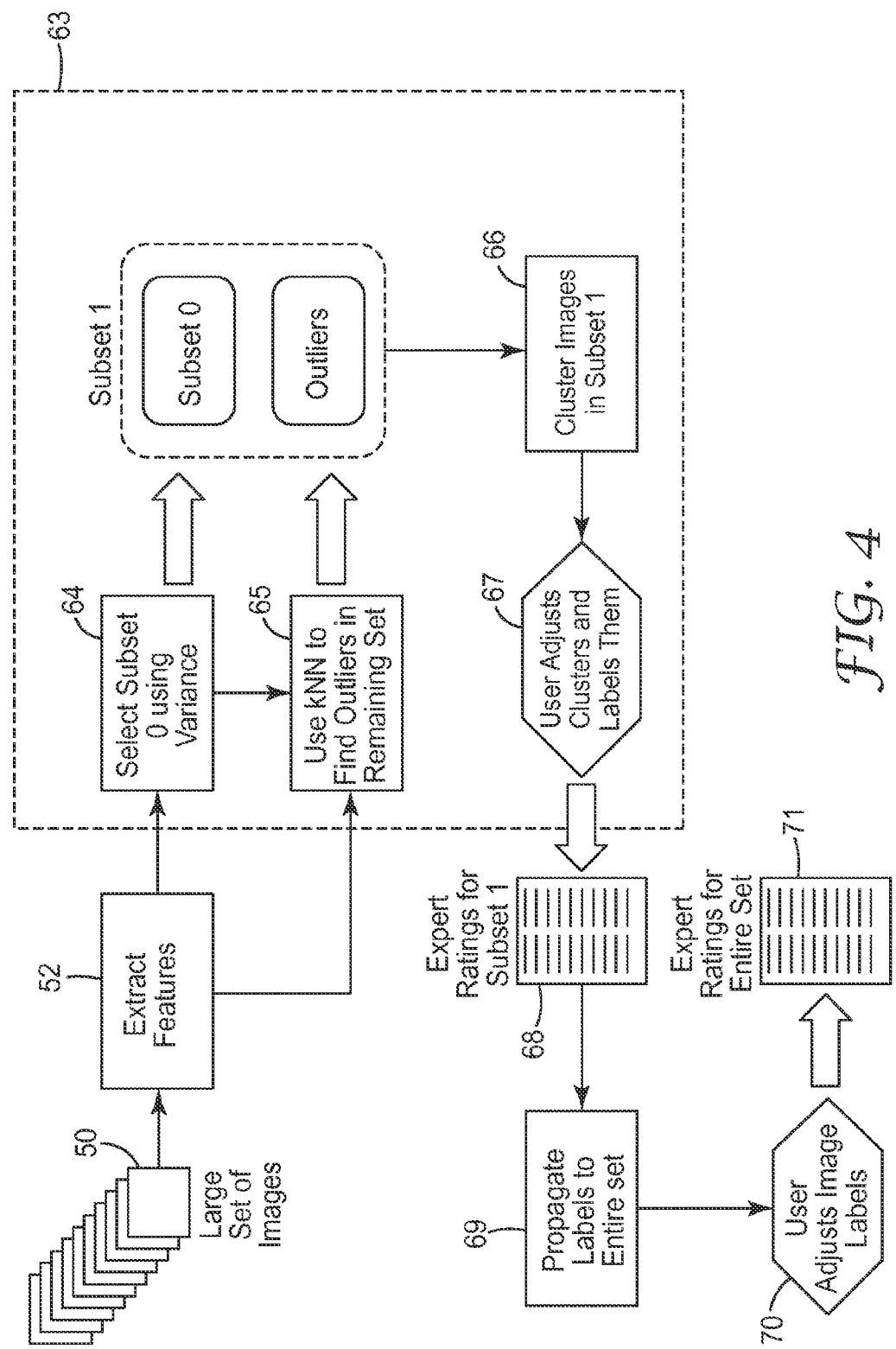
FIG. 4 is a flowchart illustrating an example operation of a software rating tool.

FIG. 4 is a flowchart illustrating an example operation of rating tool 37 in assisting experts 38 in assigning discrete ratings 53 to training data 35 (step 55 of FIG. 3). Initially, rating tool 37 receives training data 35 and the set of feature vectors extracted by the feature extraction software module as described above.

At this point, rating tool 37 enters a clustering phase (63) in which the images are clustered based on the descriptive features extracted from the images. It is not uncommon for sets of images used for training and testing classification algorithms to be very large, often on the order of tens of thousands of images. Clustering and visualizing in detail this many images is typically not practical in a short period of time and may furthermore be unnecessary, since most large datasets contain significant redundancy, so that only a representative subset needs to be analyzed in detail. For these reasons, rating tool 37 automatically selects a representative subset of the images to aid expert 38 in the labeling process (64). To assist expert 38 in actively exploring the data and identifying the types of defects present, rating tool 37 automatically selects the subset so as to contain extreme examples of the different types of defects present within training data 35, as well as examples of images with normal levels of defectiveness.

In one example, rating tool 37 utilizes variance of pixel intensities for distinguishing cases of relatively extreme defectiveness, which has been observed to be sufficient in characterizing non-uniformities (i.e., textures) in images of web-based products. Furthermore, computing pixel variance is relatively computationally inexpensive, which may be advantageous for very large sets of training images. In the case the covariance matrix descriptors outlined above, the pixel intensity variance is given in the upper-left element of the matrix $C_I$, so that no additional computation is necessary. In this example, the first step in selecting a subset is to identify the $N_1$ images with the highest variance (64). These roughly correspond to the $N_1$ most defective images in the training data 35. Since it is also important for the subset to be representative of the set as a whole, rating tool 37 also selects $N_2$ images randomly from the remaining set. This set of $N_1+N_2$ images comprises the initial subset $S_0$ (denoted "subset 0" in FIG. 3). The sizes $N_1$ and $N_2$ are selected by the user.

In addition, rating tool 37 generates the subset to include any outliers not already included in $S_0$ that are not well represented by $S_0$ (65). Each remaining image not in $S_0$ is processed to identify its k nearest-neighbors (kNNs) in a feature space using the distance function described above (eq. 4). The term "feature space" refers to the multi-dimensional space defined by the dimensions of a feature vector, such as the feature vector defined above in eq. 1. If the distances to all of its kNNs are greater than a threshold $T_d$, then the image is considered an outlier. The parameters k and $T_d$ can be configured by expert 38, although default values may be used. This allows expert 38 to try different values and view the results. Example default values may be, for example, k=5 and $T_d$=1.0. Rating tool 37 adds any outliers selected in this manner to the previously selected $N_1+N_2$ images to form the complete subset $S_1$ (denoted "subset 1" in FIG. 1).

After selecting representative subset $S_1$ of training images, rating tool 37 applies a clustering algorithm to the subset to form small groups of relatively similar images from those in subset $S_1$ (66). Rating tool 37 forms the clusters to present a more intuitive visualization of the training dataset and makes it easier for expert 38 to explore. In one example, rating tool 37 applies a bottom-up agglomerative clustering algorithm to form image clusters in subset $S_1$ according to their covariance matrix descriptors. In this process, each image is initially treated as a separate cluster and successive clusters are identified using previously established clusters. For example, based on the inter-image distances computed using (4), rating tool 37 forms an agglomerative hierarchical linkage tree, which encapsulates the hierarchical inter-relationships between the training data. Rating tree terminates the process (i.e., "cuts off" the linkage tree) at a certain point in order to generate the configured number of clusters $N_c$, as specified by expert 38. Additional information on agglomerative hierarchical clustering can be found in W. H. E. Day and H. Edelsbrunner, "Efficient Algorithms for Agglomerative Hierarchical Clustering Methods", *Journal of Classification*, vol. 1, no. 1, pp. 7-24, 1984.

Since there may be many clusters (e.g., several hundred in some cases), rating tool 37 also orders the clusters with respect to one another so that the most similar groups are displayed in close proximity to one another. This is accomplished by rating tool 37 forming a second agglomerative hierarchical linkage tree, in this case encapsulating the inter-relationships between the clusters themselves. Thus, an ordering of the clusters can be obtained by observing the lowest level (leaf nodes) of the second tree. To form the second hierarchical linkage tree, rating tree 37 analyzes the image clusters in pair-wise fashion and computes pairwise inter-cluster distances between each cluster pair. The inter-cluster distances between each of the clusters is used to form the second linkage tree. In one example, rating tree 37 computes the distance between two clusters as the median of the individual distances between the images in the two clusters. Rating tool 37 utilizes the arrangement of the leaf nodes of the second tree to control display of the image clusters, thereby displaying the most similar image clusters in close spatial proximity to one another. This aids expert 38 in forming an understanding of the defects present within and represented by the training data.

After clustering the training images by developing the linkage trees, rating tool 37 presents a user interface by which the expert is given an opportunity to visualize the clusters and re-assign images in cases where the clustering is visually unacceptable (67). The user then assigns expert ratings to each cluster of images as opposed to labeling each image independently (68), and rating tool 37 propagates these expert ratings to the remaining set of images without requiring further user interaction, thus resulting in expert ratings for the entire dataset (69). That is, the rating tool 37 applies algorithms described herein to automatically assign expert ratings to the entire dataset of training images. In other words, expert 38 need only assign expert ratings to all (or some) of the image clusters in the subset $S_1$, in each identified defect class, using the user interface provided by rating tool 37. Rating tool 37 automatically propagates these expert ratings to the remaining unlabeled images, including those images not within in subset $S_1$.

For each unlabeled image $I_u$, rating tool 37 computes the pairwise distances from this image to each labeled image $I_l$ (i.e., to each image within subset $S_1$ to which an expert ratings has been assigned) using the distance function (eq. 4). These distances are then converted to pairwise affinities according to:

$$a(I_u, I_l) = \exp\left(-\frac{d_C^2(I_u, I_l)}{\sigma^2}\right), \quad (5)$$

where the bandwidth parameter $\sigma$ is chosen according to a heuristic operating on the distances $d_C^2(I_u, I_l)$. These affinities are normalized to weights:

$$w(I_u, I_l) = P(I_u \rightarrow I_l) = \frac{a(I_u, I_l)}{\sum_i a(I_u, I_{l_i})}. \quad (6)$$

The quantity $w(I_u, I_l)$ corresponds to the probability of transitioning from image $I_u$ to image $I_l$ in a random walk through feature space and w is normalized such that $\Sigma_i w(I_u, I_{l_i}) = 1$.

Finally, the probability of image $I_u$ belonging to the expert rating e in this defect class is computed as:

$$p_e(I_u) = \sum_i w(I_u, I_{l_i}) \mathbb{I}(I_{l_i} \in e), \quad (7)$$

where $\mathbb{I}$ is the indicator function, so that $\mathbb{I}(I_l \in e) = 1$ if the labeled image $I_l$ has been assigned expert rating e in this defect class, and is zero otherwise. The probability of membership $p_e(I_u)$ is computed for each possible expert rating e, and the one with the highest probability is chosen as the Expert Rating for the unlabeled image $I_u$. Rating tool 37 repeats this process for every unlabeled image, in each defect class. Further exemplary information related to label propagation can be found in X. Zhu and Z. Ghahramani, "Learning from Labeled and Unlabeled Data with Label Propagation", CMU CALD Technical Report CMU-CALD-02-107, 2002.

Returning to FIG. 4, after expert 38 has assigned expert ratings to each cluster of images and the labels have been automatically propagated to the remaining images, rating tool 37 allows the expert to explore training data 35 and adjust the label assignments if necessary (70) to ultimately produce expert ratings for the entire set of training data 35 (71). In this way, rating tool 37 provides functionality for automatic subset selection and the subsequent propagation of expert ratings to the larger set of images within training data 35. As a result, rating tool 37 may allow experts 38 to easily manipulate and assign ratings to large datasets (e.g., on the order of tens of thousands of images) even though the images may contain significant redundancy.

Figure 5:
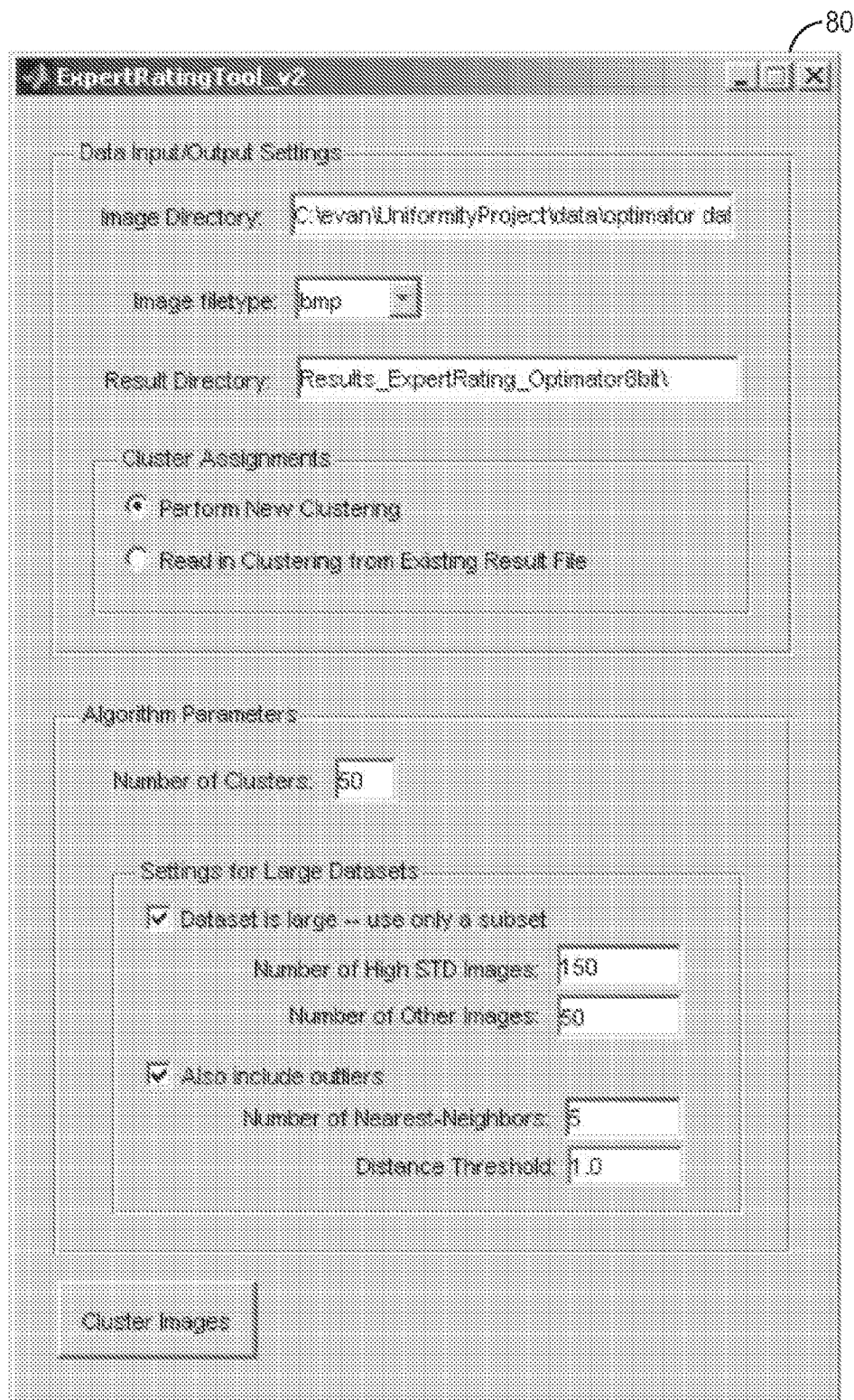
FIGS. 5-10 illustrate example features of a user interface presented by the rating tool.

FIG. 5 is an illustration of an example window 80 presented by the user interface of rating tool 37 by which expert 38 configures parameters to control the clustering process. In this example, window 80 includes input mechanisms by which expert 38 specifies a directory of the training images, the format of the training images, a directory for outputting results and a selection indicating whether the rating tool should perform a new clustering of the images or read is input the results from a previous clustering process.

In addition, expert 38 may specify certain parameters for controlling the clustering process. In particular, window 80 includes input fields for specifying the number of clusters into which rating tool 37 is to organize the training images. As described above, rating tool 37 utilizes the desired number of clusters specified by the user to truncate the clustering process upon generating the first linkage tree to have a number of leaf nodes that meet or exceed the specified number of clusters. In addition, expert 38 can specify whether training data 35 is a large dataset and that rating tool 37 should automatically identify a representative subset of images for clustering as described herein. In this case, expert 38 can also specify the parameters for controlling the size of the representative subset $S_0$, i.e., the number $N_1$ of images having the highest variance to include (150 in FIG. 5) and the number $N_2$ of images to randomly select from the remaining images (50 in FIG. 5). This set of $N_1 + N_2$ images comprises the initial subset $S_0$. In addition, expert 38 can specify whether rating tool 37 is to include outliers in the representative set $S_1$ and, if so, the number k of nearest-neighbors (kNNs) to examine in feature space for each image (5 in FIG. 5) and the threshold $T_d$ for characterizing the image as an outlier (1.0 in FIG. 5).

Figure 6:
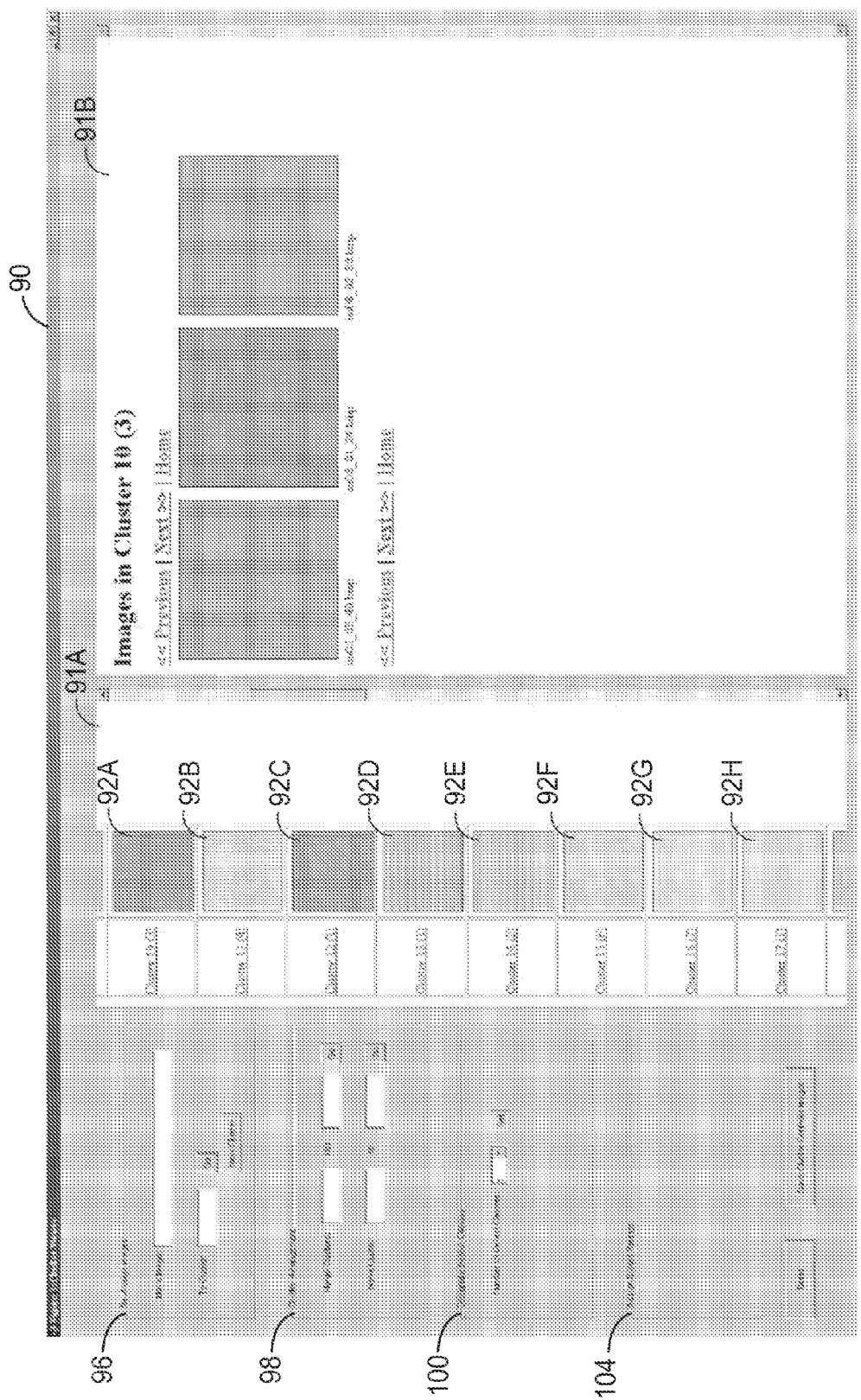

FIG. 6 is an illustration of an example cluster view window 90 presented by rating tool 37 to display the results of the clustering operation. As can be seen, the image clusters are displayed visually in two separate panels 91A, 91B, through which the user can navigate and explore the clusters using the embedded hyperlinks. Left-hand panel 91A provides a high-level overview of the clustering results by displaying a single representative (centroid) image from each clusters 92A-92N. For each cluster, panel 91A displays the representative image, an identifier associated with the cluster and, in parentheses, the number of images assigned to that cluster. For example, cluster 92A has an identifier of "10" and three images have been assigned to the cluster. Rating tool 37 arranges clusters 94A-94N within scrollable panel 91A in accordance with the second agglomerative hierarchical linkage tree described above so that clusters containing similar images are placed in close proximity to one another within the panel. In other words, rating tool 37 may arrange clusters within the scrollable panel 91A in accordance with the leaf nodes of the second agglomerative hierarchical linkage tree.

To explore in more detail, expert 38 can then select (e.g., click on) the representative image or identifier for any of clusters 92 in order to view the images contained therein within right-hand panel 91B. In the example of FIG. 6, expert 38 has selected cluster 92A (i.e., cluster having identifier "10") for review. In this example, panel 91B shows the three images that have been assigned to the cluster and all bear a strong resemblance to one another, indicating that the clustering algorithm appropriately grouped them. Due to the grouping and ordering of the images in subset S1 as presented by panel 91A, expert 28 can explore clustered training data 35 in a very intuitive manner. This may be advantageous over other techniques in which a user may simply be presented with a large unorganized collection of images for manual review and label assignment. The clustering and visualization capabilities described herein may simplify the data exploration task for expert 38, and enable the expert to quickly identify the types of defects present in the representative training data.

As shown in FIG. 6, cluster view window 90 includes input region 96 with which expert 38 interacts to modifying the cluster assignments of individual images, including the ability to move an image to either a different cluster or to a new one. In some cases, rating tool 37 records when the user indicates that an image should be re-assigned to a different cluster and uses this information to automatically update the clustering based on this new input. For example, rating tool 37 may automatically determine which images in the original cluster are similar to the moved image and, based upon this determination, also move these images to the new cluster. In addition, input region 98 allows the user to interact with the clusters themselves, including the ability to merge two clusters, and the ability to physically move a cluster to a different position in the display order. Rating tool 37 automatically updates display panels 91A, 91B in cluster viewing window 90 in real-time to reflect the changes made in the cluster assignments. In this way, rating tool 37 may be used in a manner that allows expert 38 to have the final say regarding any type of grouping or assignment of the representative images within training data 35. This also provides an extra measure of flexibility in terms of visualization, since ultimately the purpose of the clustering and ordering operations are to provide an enhanced ability to visualize and rate the training data.

In addition, cluster view window 90 includes input region 100 for defining the number of defect classes present within training data 35. Cluster view window 90 also includes input region 104 for assigning expert ratings to the images. Each of input regions 100, 102 are discussed in further detail below.

Figures 7, 8:
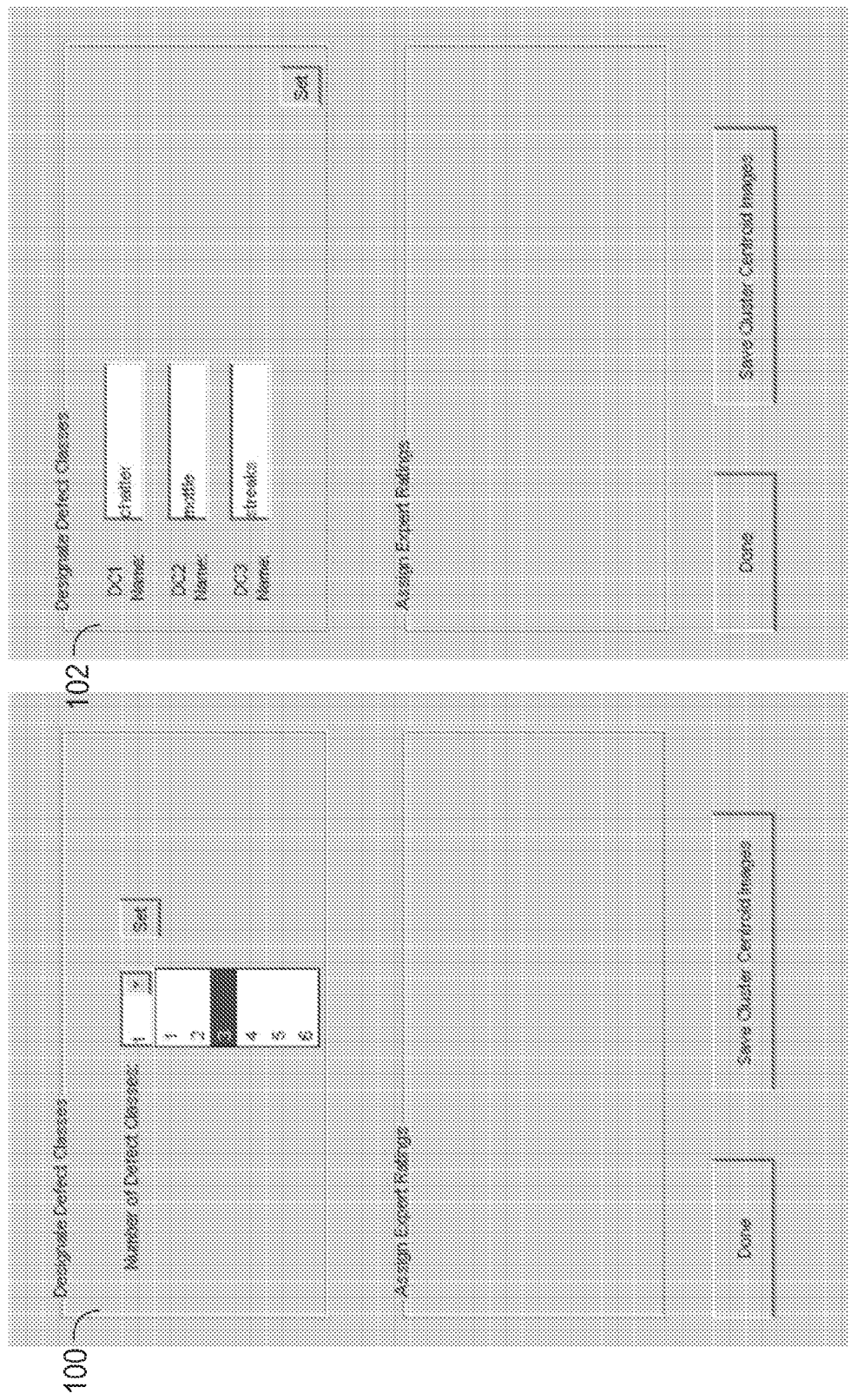

FIG. 7 shows input region 100 of viewing window 90 in further detail. In this example, expert 38 has indicated that three defect classes exist in the training data based on the review and exploration of clustered training data 35 via cluster viewing window 90. As shown in FIG. 8, once expert 38 sets the number of defect classes, cluster viewing window 90 presents another menu 102 in the same location to allow the user to enter the names of the defect classes which provide a meaningful way to identify them. In the example of FIG. 8, expert 38 has entered names of "chatter," "mottle" and "streaks" for the three types of defect classes identified within training data 35. Display panels 91A, 91B in the cluster viewing window 90 remain open while expert 38 interacts with input region 100 and menu 102, so that the expert still has the option to navigate and visualize the clustered training data while assigning the number of defect classes for the representative training data and names for each of the defect classes.

Figure 9:
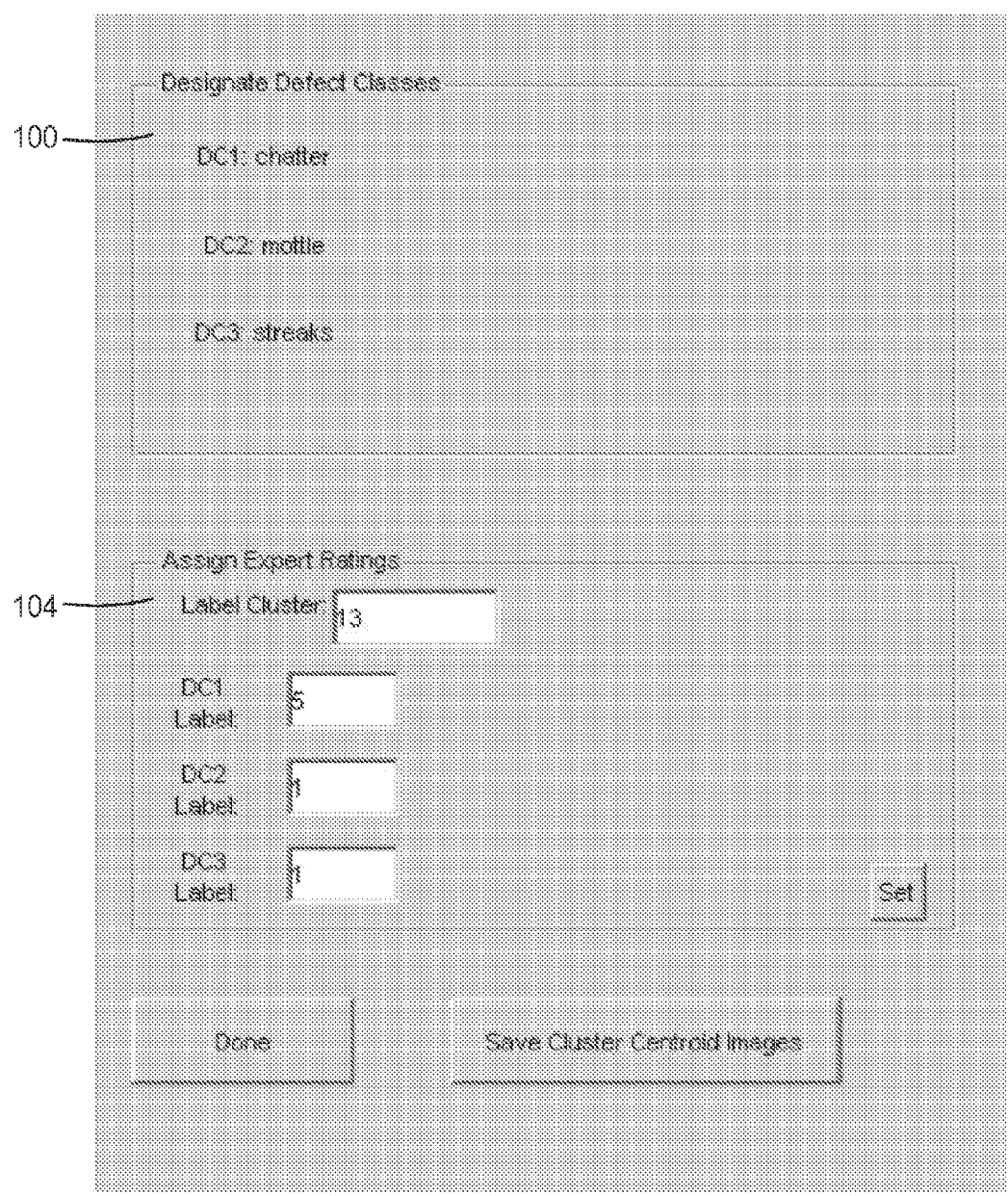

FIG. 9 shows input region 104 of cluster viewing window 90 for assigning expert rating labels to image clusters within the representative subset $S_1$ of training data 35. Once expert 38 has interacted with input region 100 and menu 102 to assign the number and names of the defect classes present in the data, rating tool 37 allows the expert to interact with input region 104 to assign expert ratings to the images of training data 35. In order to greatly simplify this task, rating tool 37 allows expert 38 to assign rating labels to entire clusters, instead of having to label individual images, which could be quite tedious and error-prone. In addition, expert 38 has the option to not label any cluster. In subsequent processing, when the labels are propagated the remaining images not in subset $S_1$, the labels are also propagated to the images in any clusters which are not labeled. As can be seen in FIG. 9, cluster viewing window 90 allows expert 38 to label all defect classes in a cluster simultaneously. For example, in FIG. 9, expert 38 has specified labels of "5", "1" and "1" for the defects "chatter," "mottle" and "streaks" within cluster "13" of the training data. Furthermore, in one example, rating tool 37 puts no restriction on the types of expert ratings that can be assigned. Labels can be numerical, such as the "1" and "5" labels shown here, or they could be textual "acceptable" and "rejected" labels. Once expert ratings have been assigned to a cluster, panel displays 91 are updated in real-time to reflect these changes.

Figure 10:
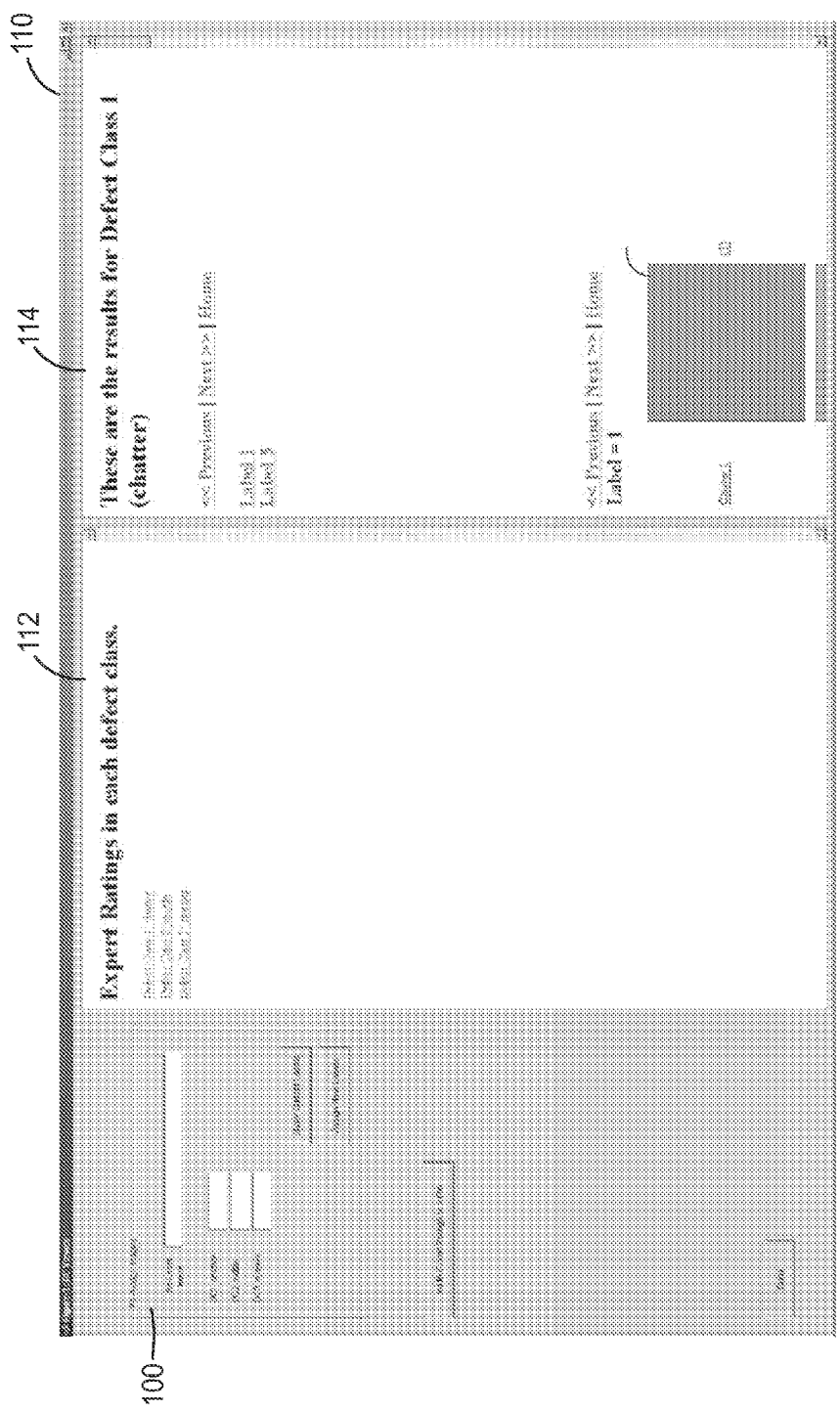

FIG. 10 is an illustration of a final expert rating viewing window 110 presented by rating tool 37 with which expert 38 can visualize and modify the expert ratings in each defect class. Expert rating viewing window 110 displays the final expert rating labels for all images. As shown in FIG. 10, expert rating viewing window 110 contains two side-by-side HTML display panels 112, 114 through which the user can visualize the results by navigating through the pages using the embedded hyperlinks. Expert rating viewing window 110 also contains menu options 120 on the left-hand side for modifying expert ratings.

In terms of visualization, expert rating viewing window 110 displays the results of the labeling process in a way that is intuitive and easy for expert 38 or other users to understand. As one example, expert rating viewing window 110 displays the results for each defect class in a separate HTML page. In each defect class, the images with each possible expert rating are shown within panel 114 as a separate part of the HTML page for that defect class. For example, as shown in FIG. 9, HTML panel 112 lists the defect classes. Upon selection of one of the defect classes, HTML panel 114 shows the images for each possible expert rating. This allows expert 38 to view defects in a cluster independent manner based on the different labels of that defect as assigned to the images. In the example of FIG. 9, the software tool presents the results in "Defect Class 1 (chatter)" starting with the images that have received a label of "1" on the top of the page. HTML panel 114 is vertically scrollable so that expert 38 may review each label utilized for the defect class and, for that label, each image assigned with that label.

To further enhance the user's ability to comprehend the data, rating tool 37 performs another clustering operation to cluster the images within each possible expert rating in a given defect class into relatively small groups of similar images. Rating tool 37 generates HTML panel 114 for the currently selected defect class (e.g., "Defect Class 1 (chatter)") which shows only the centroid image of each cluster. This helps keep only a small, manageable number of images on the display. For example, for label "1" within the "chatter" defect class, rating tool 37 has generated HTML panel 114 to display centroid image 116. Expert 38 can click on the centroid image for each cluster in order to navigate to another HTML page on which all images contained in that cluster are displayed.

With respect to the clustering operation for generating HMTL panel 114, rating tool 37 performs a separate clustering computation within each possible expert rating for every defect class. That is, as described, each image receives an expert rating in every defect class. In other words, each defect class contains all the images, but the images are in general distributed differently among the possible expert ratings in each defect class. For example, a certain image might have an expert rating of "1" in the defect class "chatter", but an expert rating of "5" in the defect class "mottle." Rating tool 37 performs separate clusterings so as to compute independent linkage trees for each label of each defect class. As one example, rating tool 37 may compute clusterings in defect class "chatter" for the images with expert Rating "1" and those with the expert rating "5," and likewise in the other defect classes.

In one example embodiment, the clusters are computed as follows. The set of images with expert rating e in defect class c is referred to as $S_e^c$. The set $S_e^c$ is made up of both images from the initial subset $S_1$, as well as other images from $\overline{S_1}$ to which the expert ratings were propagated. Images $S_e^c \cap S_1$ represent the images with expert rating e in defect class c that were in the initial subset $S_1$ that we labeled previously. Since the images in $S_1$ were clustered previously, each image in $S_e^c \cap S_1$ has already been assigned to a cluster. Rating tool 37 uses these cluster assignments to initialize the clustering of $S_e^c \cap S_1$. That is, this is used as an initial clustering to start the process, then these clusters are modified as new images are added to them sequentially. For each image in $S_e^c \cap \overline{S_1}$ (i.e., the images in $S_e^c$ that do not already have cluster assignments), we assign it to the cluster in $S_e^c \cap S_1$ to which it is closest. This procedure is more efficient than computing an entirely new clustering for each set $S_e^c$, since it exploits our previous clustering of $S_1$, and clusters the remaining images $S_e^c \cap \overline{S_1}$ incrementally.

Expert rating viewing window 110 also includes menu options 120 on the left-hand side for modifying expert ratings for any image by entering the image name. Using menu options 120, the user can both view the current expert ratings of an image in all defect classes, as well as change them if necessary.

Figure 11:
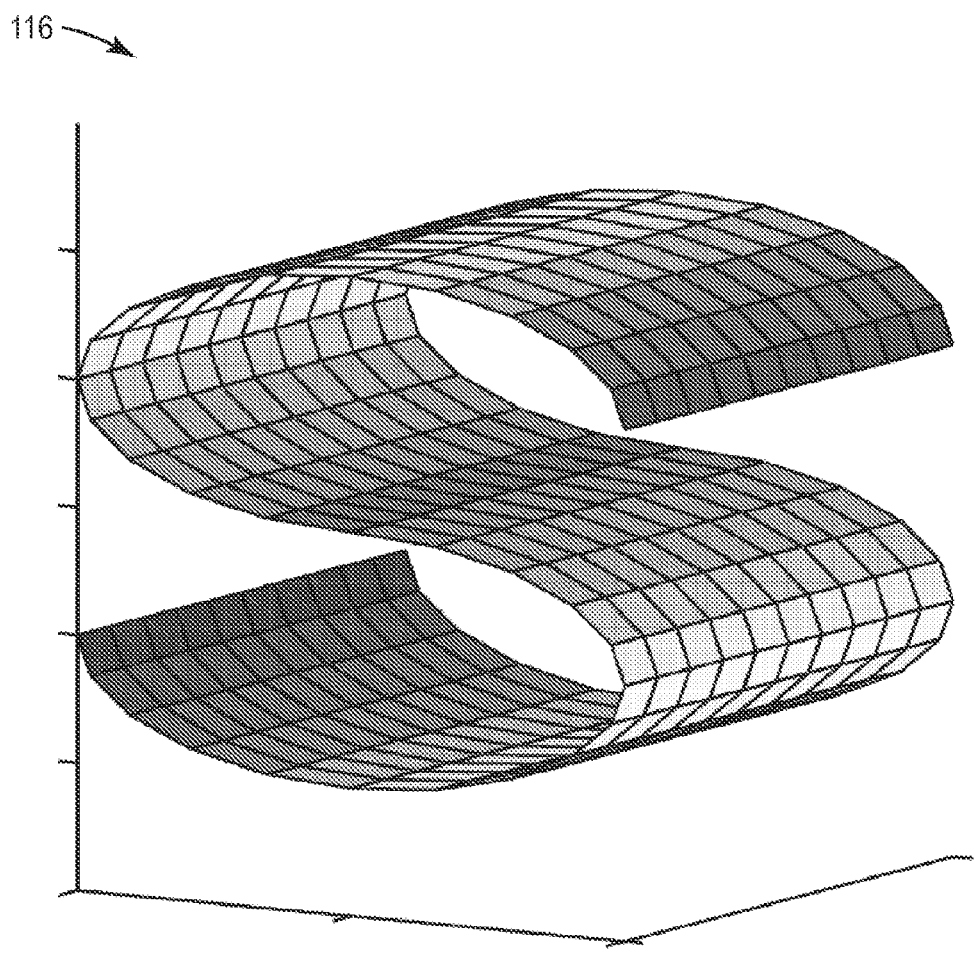
FIG. 11 illustrates a continuous three-dimensional (3D) surface, referred to as a "manifold," in reference to which the algorithms applied by the training software to produce a continuous ranking model are readily understood.

The expert ratings 53 ultimately produced by rating tool 37 can be utilized by training module 41 to generate a continuous ranking of the training images and produce continuous ranking model 34 based on the severity of their non-uniformities. FIG. 11 illustrates a continuous three-dimensional (3D) surface, referred to as a "manifold" 116, in reference to which the algorithms applied by training module 41 to produce continuous ranking model 34 are readily understood. The feature vector associated with each image can be thought of as a single point in a high-dimensional space. However, since all of the images are of the same type of material and are taken with the same imaging device or other sensor, under the same imaging conditions and geometry, the underlying number of degrees of freedom can be lower than the dimensionality of the embedding feature space. It is therefore useful to view each training image as one of the high-dimensional points lying on manifold 116 (i.e., the continuous 3D surface), or a collection of manifolds, which is embedded in this space, but which may have a lower intrinsic dimensionality (degrees of freedom) than the overall space. An illustrative example is shown in FIG. 11 for the simple case of a 3-dimensional space with a 2-dimensional object embedded in it, although in practice the dimensionality of the feature vectors is typically much higher. Further example details on manifold embeddings in high-dimensional spaces are described in H. S. Seung and Daniel D. Lee, "Cognition: The Manifold Ways of Perception," *Science*, vol. 290, no. 5500, pp. 2268-2269, Dec. 22, 2000.

As one simple example with respect to FIG. 11, a set of training images in which all of the training images show the same web material with different levels of down-web chatter. In this simple case, even though each training image may be represented by a high-dimensional feature vector that captures various texture-related characteristics, in this case there may be only one underlying degree of freedom within this set of images, corresponding to the level of chatter. As such, these training images can be viewed as points that lie on a one-dimensional manifold, e.g., a line that snakes through a curvy path in the high-dimensional space of FIG. 11.

One advantage of this representation of feature vectors as points on a manifold is that the algorithms of training module 41 exploit this underlying structure in the training data in order to make use of only the most relevant and useful information contained therein. Moreover, the embedding in lower-dimensional spaces can be useful when learning from relatively few high-dimensional feature vectors. Algorithms exist for performing manifold embedding, which is the term used herein for the task of recovering low-dimensional representations of high-dimensional data while preserving the underlying structure. Some examples of such algorithms include Self-Organizing (Kohonen) Maps, Multi-Dimensional Scaling, Isomap, and Locally-Linear Embedding. One example algorithm is Diffusion Maps, as described in further detail below. Further details on Diffusion Maps can be found in S. Lafon and A. B. Lee, "Diffusion Maps and Coarse-Graining: A Unified Framework for Dimensionality Reduction, Graph Partitioning, and Data Set Parameterization," IEEE Transactions on Pattern Analysis and Machine Intelligence, vol. 28, no. 9, pp. 1393-1403, September 2006.

Given the representation of each training image as a point on a manifold in feature space, the algorithms of training module 41 perform a discrete random walk around the feature space. During this random walk, for each time step, the random walker can move from one point on the manifold to another, without ever leaving the manifold. In this context, the algorithms compute the probability of transitioning from a point on the manifold to all other points. In general, this transition probability is typically higher for nearby points in the manifold and lower for distant points. However, the algorithms take into consideration the expert ratings, penalizing for transitions between points with different discrete labels. These transition probabilities are then used to propagate the expert ratings from each point to all the surrounding points, so that every point ends up with some fraction of the discrete labels from the other points, which allows us to compute a continuous severity value for each point corresponding to one of the training images along the continuous surface. Both the extracted features and the provided (expert) rankings are exploited at this stage.

Figure 12:
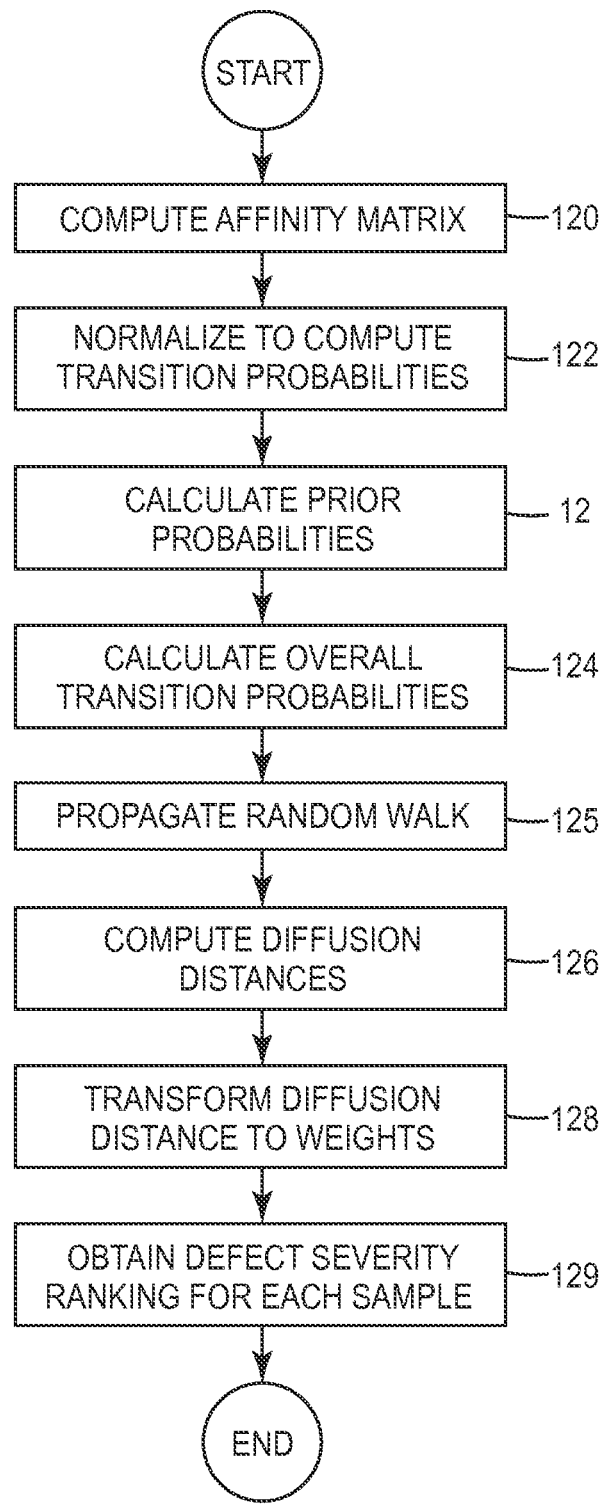
FIG. 12 is a flowchart showing in more detail an example process by which training software processes feature vectors extracted from training images to develop a continuous ranking of the training images and produce a continuous ranking model.

FIG. 12 is a flowchart showing in more detail an example process by which training module 41 processes the feature vectors to learn a continuous ranking of the training images and produce continuous ranking model 34.

First, training module 41 computes an affinity matrix K of size N-by-N, where N is the number of training samples (step 120). For example, to learn a continuous ranking of the N training images, the set of feature vectors are defined as $x_1, x_2, \ldots, x_N$, with corresponding expert ratings $c_1, c_2, \ldots, c_N$. Each discrete rating is assumed as either a "1," "3," or "5," i.e., $c_i \in \{1, 3, 5\}$, where a "1" is a sample that is acceptable, and a "5" is a sample that is clearly unacceptable. The expert ratings can be either more or less finely discretized than this, and the algorithms are not limited to this particular example. Given the feature vectors, training module 41 computes the affinity matrix K of size N-by-N, where each element can be given, for example, by $$k(i,j) = \exp(-\|x_i - x_j\|^2/\sigma^2). \tag{8}$$

The affinity matrix gives a measure of similarity between each pair of training samples in feature space, and others different than (eq. 8) can be used, e.g., polynomial ones. The bandwidth parameter σ defines how quickly the exponential decays as the distance between a pair of points increases. In practice, a local parameter σ is estimated for each training sample according to a heuristic, such as the median distance to its k-nearest neighbors. In this case, the denominator of Equation (8) becomes the product of the local bandwidths corresponding to samples $x_i$ and $x_j$.

The distance used in the affinity matrix can be simply the Euclidean distance as in the example in (8) or more sophisticated ones, depending on the features, such as covariance distances or Kullback-Leibler distances.

Next, from the affinity matrix, the transition probabilities can be calculated (step 122) according to:

$$p_a(i,j) = k(i,j)/\Sigma_l k(i,l), \tag{9}$$

which corresponds to the probability of transitioning from $x_i$ to $x_j$ on a random walk in feature space, based only on the affinities between points. This is a normalization of the affinity matrix K, which ensures that its rows are valid probability distributions (i.e., sum to one).

In order to take the discrete labels given by the expert ratings into account, training module 41 compute the prior probabilities of transitioning from $x_i$ to $x_j$ $$p_b(i,j) = \exp(-|c_i - c_j|^2/\sigma_p^2), \tag{10}$$

where $\sigma_p$ is a bandwidth parameter for this prior probability term (step 123). The expression for $p_b(i,j)$ penalizes more heavily for expert ratings that are farther part, so that the choice of the numerical values assigned to discrete labels is important in this context.

Training module 41 then computes the overall transition probability for each pair of training samples by the product of $p_a(i,j)$ and $p_b(i,j)$ (in step 124), $$p(i,j) = p_a(i,j) p_b(i,j). \tag{11}$$

The components of the automatic diffusion matrix and the penalty for violating expert ratings may be combined in other ways. Collectively, the overall transition probabilities p(i,j) form the matrix P. Each entry in P represents the probability of transitioning between the corresponding pair of points in one time step.

Training module 41 propagates the random walk transition probabilities for t time steps by raising the matrix P to the power t (step 125)

$$P_t = P^t, \tag{12}$$

where $P_t(i,j)$ corresponds to the probability of transitioning from $x_i$ to $x_j$ in t time steps. The number of time steps t has no physical meaning, but is a configurable parameter that can be set in the software application by the user.

Based on these transition probabilities, training module 41 computes diffusion distances (step 126). Each such distance is a measure of dissimilarity between each pair of points on the manifold. Two points are assigned a lower diffusion distance (i.e., are said to be closer together in diffusion space) if their distributions of transition probabilities are similar. In other words, if their respective rows of the matrix $P_t$ are similar to one another, the two points are assigned a lower diffusion distance. In one example, the squared diffusion distances are computed according to the equivalent expression:

$$d^2(i,j) = \Sigma_l \lambda_l^{2t} (\psi_l(i) - \psi_l(j))^2, \tag{13}$$

where i.e., $P\psi_l = \lambda_l \psi_l$, i.e., $\psi_l$ and $\lambda_l$ are the eigenvectors and eigenvalues of P, respectively. This may avoid the use of resources associated with explicitly raising the matrix P to the power t, which can be a computationally expensive operation if numerous training samples are available. Fast techniques for computing eigenvectors can be used, in particular those developed to compute the first eigenvectors corresponding to the largest eigenvalues.

These diffusion distances, which are proportional to the dissimilarity between pairs of samples, are converted by training module 41 to weights (step 129) that are proportional to the similarities according to:

$$w(i,j) = \exp(-d^2(i,j)/\sigma_w^2)/\eta, \tag{14}$$

where $\sigma_w$ is another bandwidth parameter, and η is simply a normalization constant which ensures that rows of the weight matrix W sum to one. Finally, training module 41 generates continuous ranking model 34 ("model 34") by computing the non-uniformity severity ranking value for each of the training samples $x_i$ (step 130) by:

$$r_i = \Sigma_j w(i,j) c_j. \tag{15}$$

The resulting ranking value $r_i$ is a weighted average of the Expert Ratings of all the training images. However, even though the expert ratings may be highly discrete (e.g., "1", "3", or "5"), the ranking values are on a continuous fine scale. Furthermore, the algorithm parameters can be adjusted by a user interface so as to give a ranking which is continuous overall. The weights in (eq. 15) are derived by the diffusion distance process that combines automatic image/feature comparisons with expert rankings. Other ways of normalized weighting can be considered, e.g., exponential weighting functions.

The process described above with respect to FIG. 12 can override incorrect labels in the expert ratings. That is, if the expert had mistakenly labeled a certain image as, for example, a "1" instead of a "5", the process could still assign this point a ranking value closer to the other "5" points. This is primarily due to the influence of the two different terms in the product of Equation (14). While the second term takes the discrete labels into account, the first term is based only on the intrinsic structure of the data on the manifold. The relative effects of these terms are controlled by their respective bandwidth parameters. If $\sigma_p$ is set to a large value, then the prior probability term will have very little influence on the transition probabilities.

Further, multiple experts can be combined as well. In this case, training module 41 utilizes an additional weight on the computation of the affinity matrix for each one of the experts. Reliability of the different experts can be assessed in the same fashion.

Figure 13:
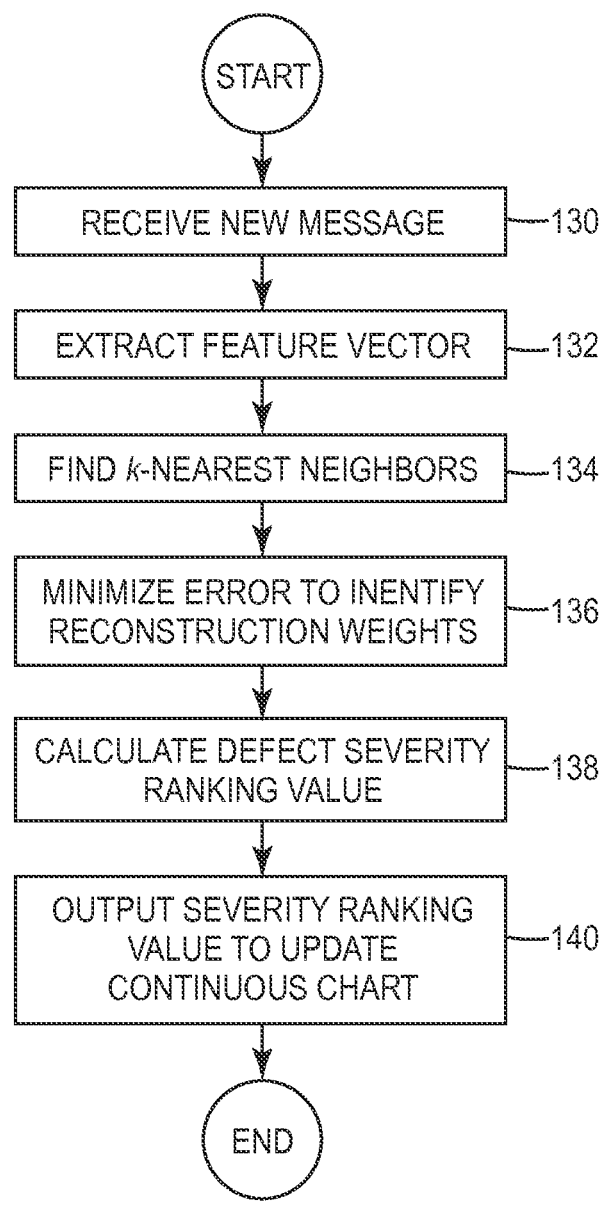
FIG. 13 is a flowchart showing in more detail an example process by which a charting module utilize the continuous ranking model in real-time to detect the presence of non-uniformity defects and to provide a continuous charting of a severity level for each defect.

FIG. 13 is a flowchart showing in more detail an example process by which charting module 39 utilize continuous ranking model 34 ("model 34") in real-time to detect the presence of non-uniformity defects and to provide a continuous charting of a severity level for each defect.

As a new image of the web being produced is captured (130), features are extracted in the same way as for the training images (132). Specifically, given the feature vectors of the training samples $x_1, x_2, \ldots, x_N$, along with corresponding ranking values learned in the training phase $r_1, r_2, \ldots, r_N$, the function of the real-time charting module 39 is to estimate the ranking value for a new feature vector $x_q$ extracted from the new image, which is referred to herein as the query sample.

Initially, charting module 39 locates the k-Nearest Neighbors of $x_q$ among the training samples $x_1, x_2, \ldots, x_N$ for a given defect (134). In one embodiment, charting module 39 uses the Euclidean distance in feature space to find the nearest neighbors, given by:

$$d_i = \|x_q - x_i\|_2. \quad (16)$$

Figure 14:
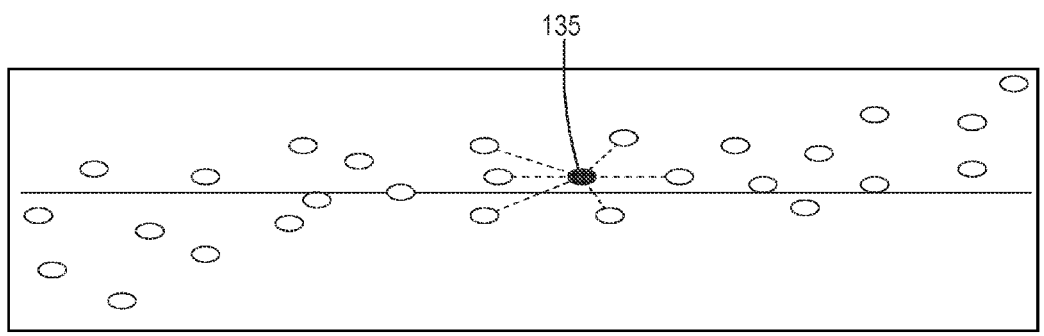
FIG. 14 is a graph providing a logical representation of finding the k-nearest neighbors in a 2-dimensional feature space.

Charting module 39 may present an interface by which the user is able to specify the number of nearest neighbors, k, as a configurable parameter. FIG. 14 is a graph providing a logical representation of finding the k-nearest neighbors in a 2-dimensional feature space. In this example, six nearest neighbors are identified for query point 135 within the feature space.

Several techniques may be used to locate the k-nearest neighbors. One technique is to perform an exhaustive search by computing the distance from $x_q$ (the query point) to each sample $x_1, x_2, \ldots, x_N$ in the training set. However, this type of exhaustive search can be computationally expensive, especially if the number of training samples is large and the feature space is high dimensional. Two other techniques are described. One is an exact search, i.e., the technique returns the same results as an exhaustive search but in a more efficient manner, and the other an approximate search. Both techniques provide significant improvement in terms of computational overhead in comparison to the exhaustive search. Any k-nearest neighbor search methods can be used, these just represent two examples.

One technique for performing a more efficient k-Nearest Neighbors (kNN) search, but which still gives the same results as the exhaustive search, is to first organize the training samples $x_1, x_2, \ldots, x_N$ into a "ball tree." The ball tree is a data structure which organizes the training samples into hierarchical groupings based on their proximity in feature space. At the lowest level of the tree, each "leaf" node will contain one or several samples which are close together. As charting module 39 progresses higher up the tree, the groupings contain larger numbers of points, but still grouped based on proximity. Finally, at the top of the tree, the "root" node contains all points in this training set. Note that this structured is computed only once for the training samples, and then will be used multiple times for the queries. Further details on use of a ball tree are described in A. W. Moore, "The Anchors Hierarchy: Using the Triangle Inequality to Survive High Dimensional Data," Proceedings of the 12$^{th}$ Conference on Uncertainty in Artificial Intelligence, pp. 397-405, 2000.

Once the training samples are organized in this hierarchical ball tree, they can be searched efficiently to find exactly the kNNs of a new query point. The algorithm for performing this search can be recursive, and exploits the intrinsic structure of the training data in order to search it efficiently. For example, if it is known that the query point $x_q$ is close to one particular node in the ball tree, then charting module 39 does not waste time to continue searching for the kNNs of the query point in another node far away. The computational price for this increased efficiency at search time is in the complexity of building the tree, which contains only the training samples and can thus be constructed offline.

Figure 15:
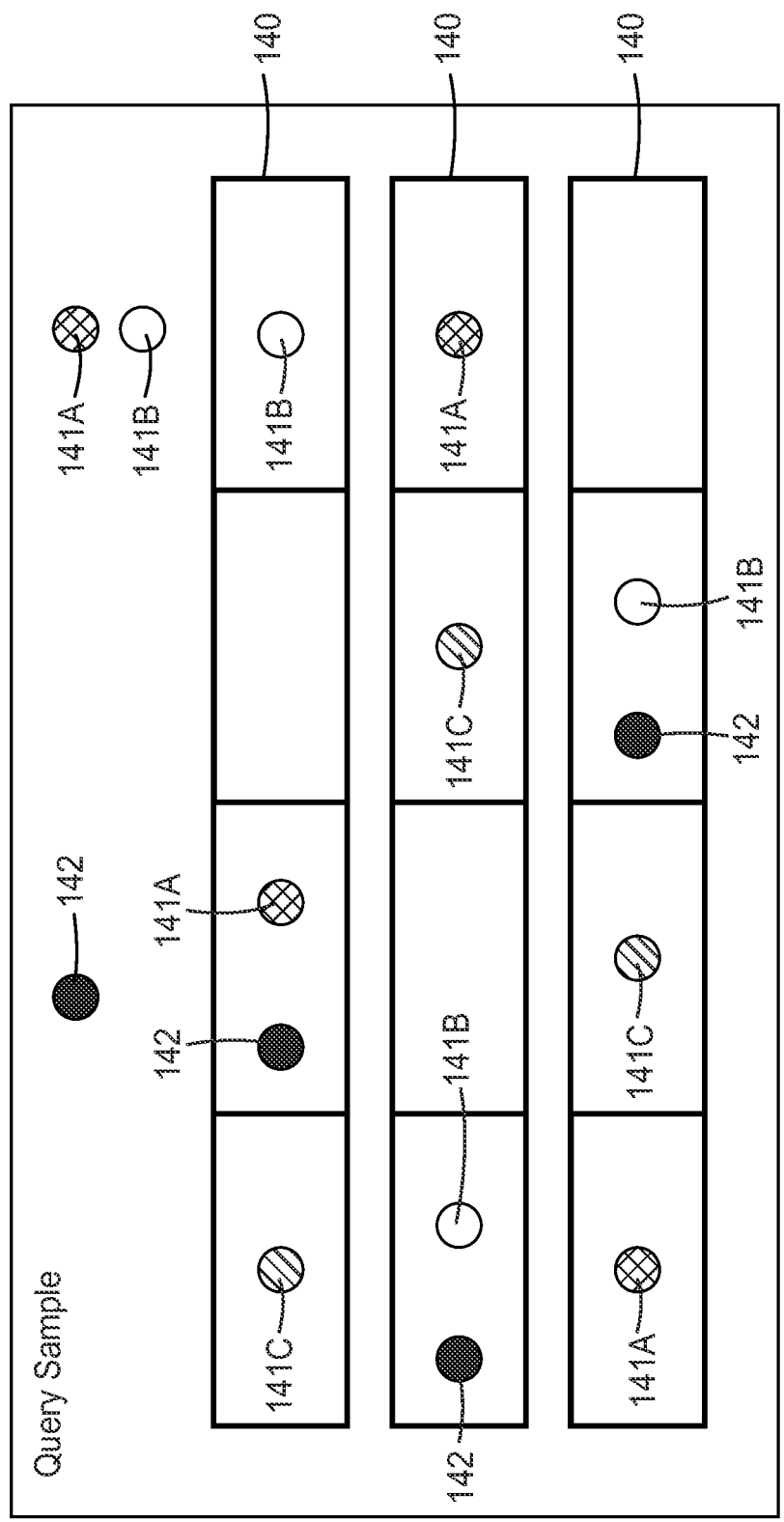
FIG. 15 illustrates a second technique for finding the k-nearest neighbors using a hashing algorithm.

As a second example, further computational efficiency can be achieved by using approximate kNN searches, which are designed to give results close to those of the exhaustive search, although they are not guaranteed to be exactly the same. One such approach is Locality-Sensitive Hashing (LSH). As before, charting module 39 organizes the training samples based on their structure in feature space in order to enable rapid kNN search. In this case, several hash tables are formed that index the training samples. Each hash table is formed by taking a random projection of the training samples, resulting in a one-dimensional representation for each sample, and then binning the samples along this line into a set of discrete groups. Repeating this procedure, several hash tables are formed and the approximate kNNs of a point can be quickly found with high probability based on these hash tables. An illustration of this is shown in FIG. 15, for the simple case of three hash tables 140 into which each of the three training samples 141A, 141B and 141C and the query sample 142 are hashed. In this case, indexing the resulting hash tables results in correctly identifying the two nearest-neighbors 141A, 141B of the query sample. Further details on Locality-Sensitive Hashing (LSH) are described in "Locality-sensitive hashing: A. Andoni and P. Indyk, Near-Optimal Hashing Algorithms for Approximate Nearest Neighbor in High Dimensions," Communications of the ACM, vol. 51, no. 1, pp. 117-122, January 2008.

Returning to the flowchart of FIG. 13, after identifying the k-Nearest Neighbors, charting module 39 computes the reconstruction weights for the query point that best express the query point as a linear combination of its k-nearest neighbors (136). The weights can be either positive or negative, and can be computed by minimizing the following error:

$$\epsilon = \|x_q - \Sigma_{i \in \Omega} w_i x_i\|_2, \quad (17)$$

where the $w_i$'s are the reconstruction weights, and $\Omega$ is the set of k-nearest neighbors. The error function (17) can be minimized in closed form. The weights can also be computed in a closed form.

Next, charting module 39 computes the severity ranking value of the query point for the particular defect as the weighted average of the ranking values of its k-nearest neighbors for that defect (138). In one example, the severity ranking value can be calculated as:

$$r_q = \Sigma_{i \in \Omega} w_i r_i. \quad (18)$$

As before, the non-uniformity severity ranking value of the query point is on a continuous scale. This approach allows the query point to receive a ranking value that is close to those of the most similar images in the training set. It is contemplated that other out-of-sample techniques can be used instead of the nearest-neighborhood technique.

Finally, charting module 39 outputs the computed severity ranking value to the operator (140). The output may take the form of updating a chart so as to show a trend in the severity ranking for the defect, or charting module 39 may simply output the severity ranking value as a single number. For example, charting module 39 may update a chart upon processing each new image so as to graph the severity level of the non-uniform defect for the web material over time. The computerized inspection system or other component may subsequently receive input from the user specifying a change to a process control parameter for the manufacturing process, and may adjust the process control parameter in response to the input. Additionally, the user may view live images captured from the web or filtered version of the images that enhance visualization of the defect. For instance, a Gabor filter or other processing filter may be applied. The filters available to the user may be based on the filter(s) used to extract features from the training images when developing the model. In this way, the user may adjust process parameters and view the effects of the adjustments with respect to specific non-uniformity patterns by viewing the filtered images obtained in real-time from the web.

Figure 16:
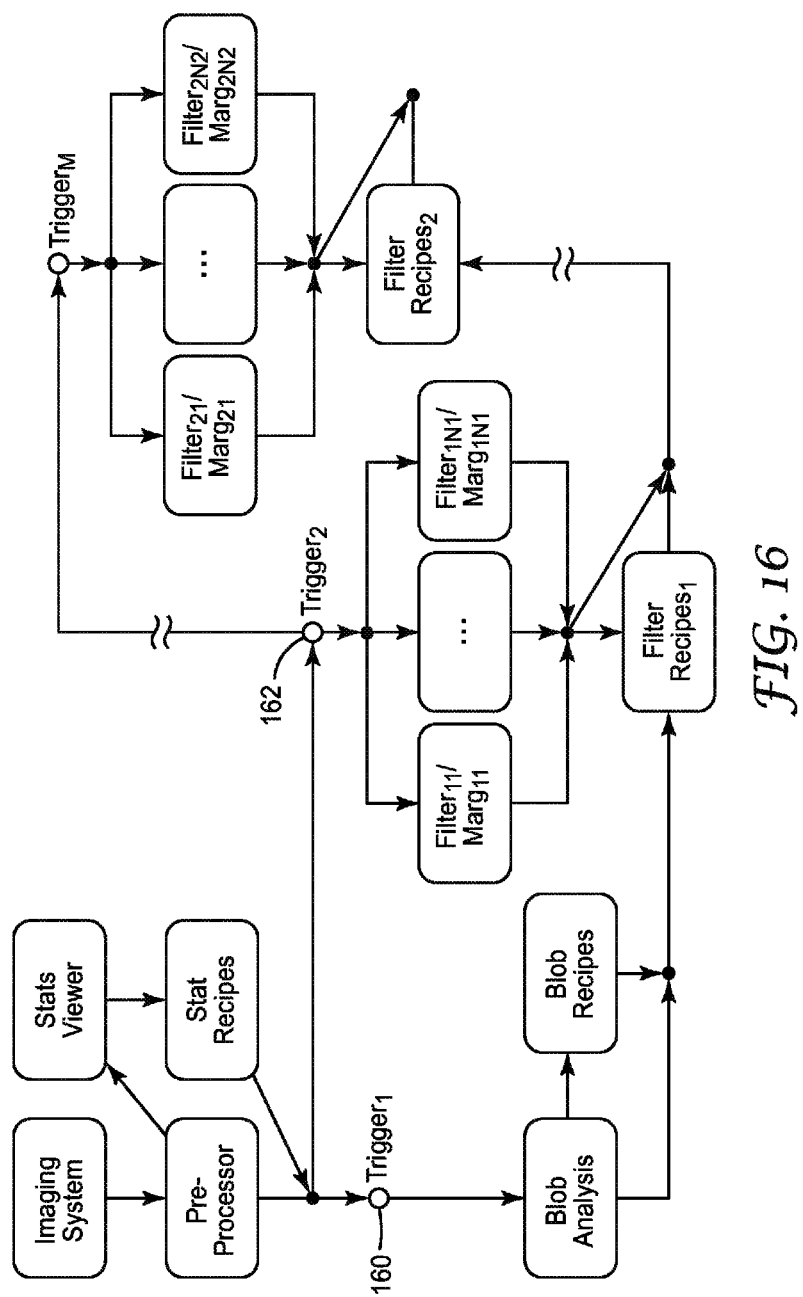
FIG. 16 is a flow diagram showing an example a dynamic system architecture in which a feature extraction module builds a "best feature set" in real-time by using the results from successively larger feature sets to trigger additional feature computations.

FIG. 16 is a flow diagram showing an example a dynamic system architecture in which feature extraction module 43 of analysis computer 28 processes streams of image data from acquisition computers 27 to dynamically determine which image features to compute on a per-image basis in real-time during manufacture of web material 20. As shown, feature extraction module 43 dynamically builds a "best feature set" in real-time by using the results from successively larger feature sets to trigger additional feature computations.

After capturing a new image of the web material, analysis computer 28 may perform some pre-processing, such as edge trimming, flattening, or the like, and compute some certain statistics for logging or output display presentation. Next, feature extraction module 43 reaches a first trigger point 160 where the decision is made whether to trigger additional processing by analyzing the features computed for the new image up to that point in the flow. For example, feature extraction module 43 may apply a base feature set that has been identified by the operator as simpler and faster processing in comparison to the other feature extraction computations. At trigger point 160, feature extraction module 43 may apply some morphological (blob) analysis using so called blob recipes to detect point defects using the base feature set. In parallel, feature extraction module 43 determines whether the base feature set provides sufficient evidence to assess non-uniformity variation within the new image within a level of confidence. For example, the decision regarding whether or not to trigger more features in order to help classify the current image can be made according to a simple heuristic. For example, one may set a simple decision rule such that, if an expected reduction in cost of misclassifying the image with respect to the non-uniformity defect from adding the dynamically determined next-best set of features is above some threshold, then feature extraction module triggers extraction of the additional features. The expected reduction in cost, i.e., the required level of confidence, can be determined using the learned Markov model, as further described below. If not, feature extraction module 43 proceeds to trigger point 162 and triggers successively more complex processing. That is, at second trigger point 162, feature extraction module 43 performs a second set of feature extraction computations, .e.g., image filtering/marginalization, in order to extract additional features. This second set of feature extraction computation may be more complex and computationally intensive than the base feature set initially performed. Feature extraction module 43 again attempts to identify and degree and type of non-uniformity using image recipes, also referred to as classifiers, which are mathematical models whose inputs are some or all of the features extracted for the new image up to this point in the flow.

The processes repeats as a chain of trigger points, where at each trigger point the decision is made whether additional, more complex, image processing computations are necessary in order to determine the degree at which any type of non-uniformity exists within the image. This determination at each trigger point is made based on the features computed for the new image up to that point in the flow.

In some situations, a sample image captured in real-time from the web material may contain multiple patterns. In accordance with the process set forth in FIG. 16, feature extraction module 43 operates such that the features that are likely to enable the most accurate classification of any non-uniformity are triggered. This process may be performed for every individual sample imaged by the computerized inspection system. Alternatively, feature extraction module 43 may operate under a polling scheme, in which the necessity to trigger or retract process components is checked after every X samples, where X is a configurable parameter.

In one example, feature extraction module 43 is configured to operate in accordance with a controlled Markov model for dynamic triggering. In this embodiment, feature extraction module 43 includes configuration data that defines a state vector x(t) which serves as a sufficient summary of information at any triggering step t relevant to future triggering events. For completeness, a triggering event any point in the process for analyzing a single image sample where feature extraction module 43 has an opportunity to select additional features to compute.

In one example, the state vector is defined through a family of classifiers $\{\Phi_i(t)\}_{i=1}^N$, where at triggering step t, $\Phi_i(t)$ only depends on the features triggered at step t and classifier family at the previous step $\{\Phi_i(t-1)\}_{i=1}^N$. An example of how such a sequence of classifier families may be constructed using the ROC-optimal classifier enhancement algorithm is described in PCT International Pub. No. WO/2010/059679. In this example, the binary classifier consists of a set of decision rules (i.e., thresholds on possibly multiple variables) that are learned from labeled training data. However, in general any discrete classification algorithm could be used. Other examples included Support Vector Machines (SVM), Logistic Regression, or Decision Trees.

With respect to defining the state vector of feature extraction module 43, the $i^{th}$ element of the state vector at step t is taken as the classification assigned by $\Phi_i(t)$, i.e. $x_i(t)=\Phi_i(t)$. One example is binary classification, so that $x(t) \in \{0, 1\}^N$, however, the method discussed herein can be extended to the multinomial case.

The configuration data of feature extraction module 43 includes a control variable that determines the action at a given trigger event, i.e., the additional set of one or more features not already computed that are designated to be computed next. To simplify the discussion, it is assumed a single feature f is to be selected at each trigger event. However, the algorithm is similar if f is taken to represent a plurality of features instead. Since the classifiers determine the state vector through judgments on the current sample image, and they only depend on f and the family of classifiers at the previous step, feature extraction module 43 computes a prediction of a future state vector on the basis of the current state vector using the conditional distribution $P_f(x(t+1)|x(t))$ parameterized by the control f to be optimally chosen. That is, $P_f$ is referred to as the transition function of the Markov chain. Feature extraction module 43 estimates the transition function in order to implement a control strategy. Given a training set of sample images and associated sequence of classifier families, feature extraction module 43 may be configured to use a simple histogram estimate $\hat{P}_f$, where $\hat{P}_f(x(t+1)|x(t))$ is the number of training samples for which the state at step t is x(t) and the state at step t+1 is x(t+1) when feature f is selected. To avoid problems associated with high dimensions, including noisy $\hat{P}_f$ and sparse sampling of the space, N may be selected to be small. Alternatively, feature extraction module 43 may be configured to utilize parameterization or kernel smoothing of $\hat{P}_f$.

With these components in place, feature extraction module 43 dynamically selects f at any triggering event utilizing the transition function estimate to choose an f that minimizes some expected loss. For example, assume a value $c_{a|b}$ is assigned as a cost of misclassifying an a as a b (with a,b $\in$ {0, 1}), then if $x_t(t)=1$, the expected loss of using classifier I is made under the assumption that it is a mistake (i.e. the true class is 0). This gives an expected loss $c_{1|0}p_t(0)FA_f^i$ where $p_t(0)$ is the prior probability any given sample is truly 0, and $FA_f^i$ is the false alarm rate ($p_t(0|1)$) of classifier I (explicitly indexed by current control f to emphasize the dependence). Similarly, when $x_t(t)=0$, the expected loss of using classifier I is $c_{0|1}p_t(1)(1-CD_f^i)$ where $CD_f^i$ is the correct detection rate $p_t(1|1)$ of classifier i. The loss function can be expressed as.

$$C_t(x,f)=\min\{c_{1|0}p_t(0)\min_{i:x_f=1}FA_f^i, c_{0|1}p_t(1)\min_{i:x_f=0}(1-CD_f^i)\}$$

As one example, feature extraction module 43 utilizes a control strategy that minimizes the total expected cost over all trigger events $\Sigma_t c_t(x,f)$. This problem can be solved exactly via dynamic programming if the sizes of the state and control spaces are not too large. Alternatively a greedy heuristic may applied at each step, selecting $f_t^* = \min_f c_t(x,f)$, to find a reasonable sub-optimal solution. In one embodiment, all possible trigger event trajectories are computed offline and feature extraction module 43 is programmed to use a look-up table online. In this way, it is possible to reduce the number of features computed for each sample image using a controlled Markov chain model for triggering the most discriminative features for the current sample. Thus, the features selected in response to any triggering event may be dynamically determined based on the currently extracted features and computed transition function.

The techniques described above can easily be extended to the multi-classifier case using, for example, a simple sum of single classifier loss functions. Also, $c_{a|b}$ can be scaled differently for different defect categories to capture relative importance or include an additive factor corresponding to feature dependent computation time. Further, the techniques above have been explained with respect to an example cost function. Other possibilities exist. For example, one might also consider a cost function that penalizes entropy of the class posterior distribution.

EXAMPLE

A simulation study was conducted using film images collected from a process development line. The complete sample set contains 8767 images that exhibited a variety of non-uniformities. Broadly, the non-uniformities can be grouped into seven categories. In addition to the chatter and (large) mottle categories, there are small mottle, bar marks/banding, splotches/watermarks, streaks, and diagonal variation defects. A sequence of classifier families were designed for each separate category. That is, seven different Boolean classifier family sequences (one for each non-uniformity category) were designed that determine presence/absence of a non-uniformity by thresholding selected features from a set 26 statistical and spectral features extracted using histogram and Gabor filter processing. The classifiers designed in accordance with the techniques described in PCT International Pub. No. WO/2010/059679 and were trained on the complete sample set.

Each classifier family sequence was designed to contain successively more complex classifiers (i.e. using more features), where each successive classifier in a give family sequence tended to assign the non-uniformity to its targeted category with higher accuracy. A trigger event was defined as the advancement of a single selected classifier family to the next most complex set of classifiers in its sequence. This corresponds directly to computing an additional set of features for the current sample at each trigger event, since it is additional features that enable the advancement in a classifier family sequence.

Figure 17:
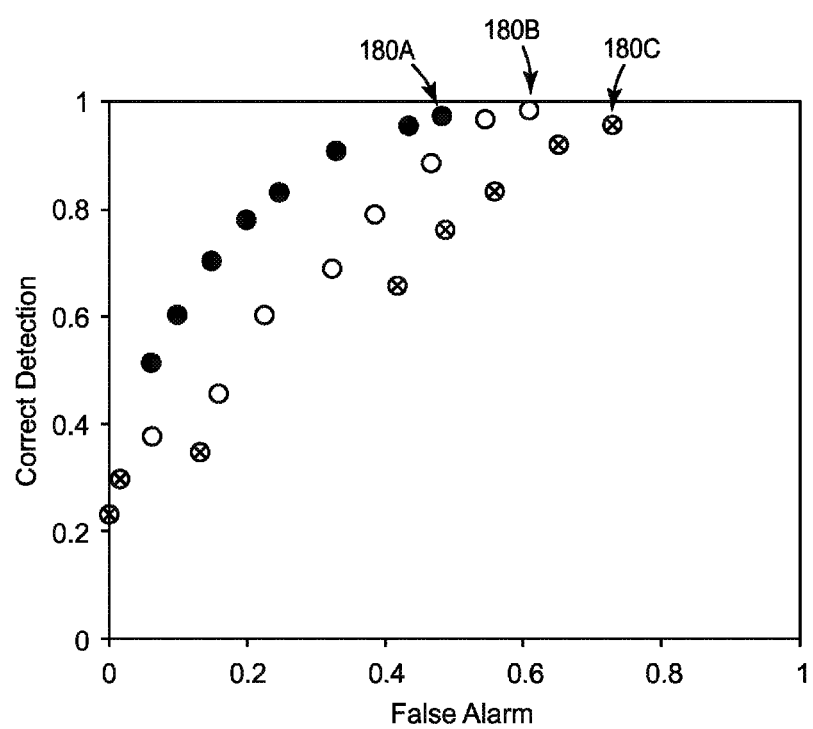
FIG. 17 shows the performance of a three-step sequence in ROC-space.

FIG. 17 shows the performance of a three-step sequence in ROC-space. As shown, each family 180A, 180B and 180C consisted of eight classifiers. The fact that the sequence is approaching the upper left corner of the ROC plot indicates improving performance at each step (red, then green, then blue).

Figure 18:
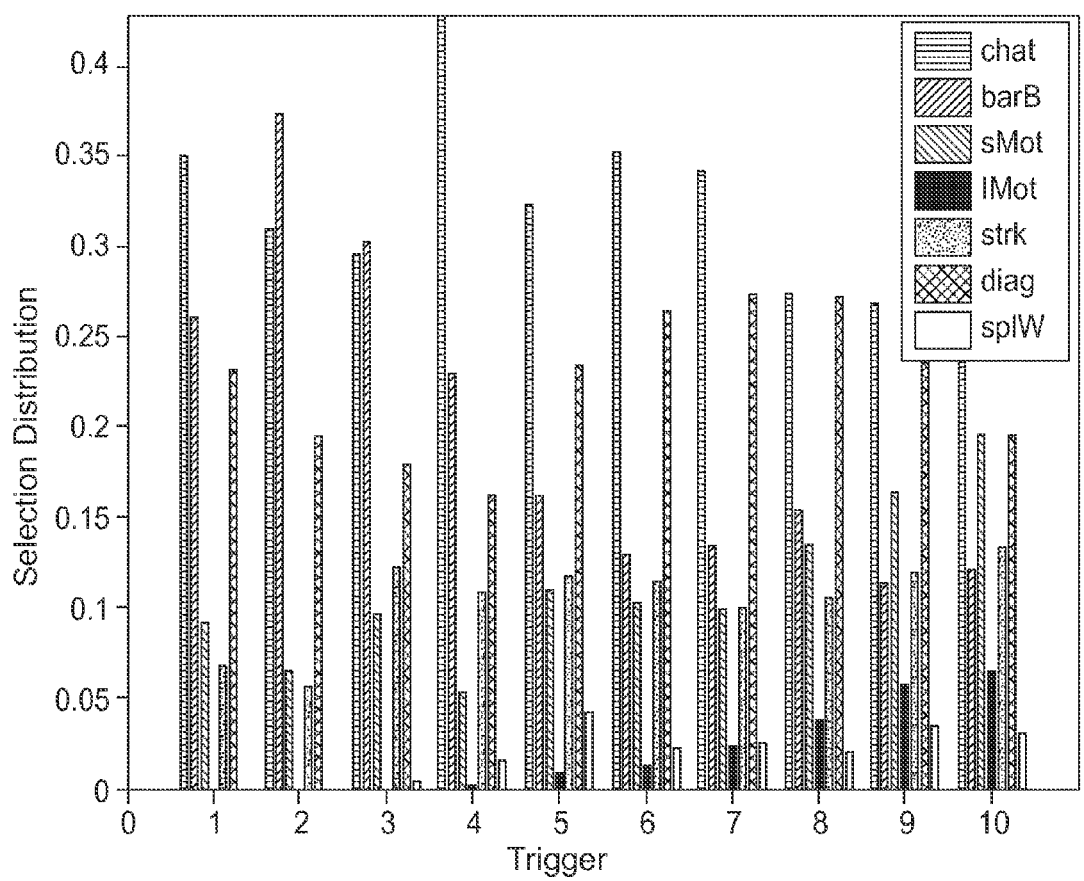
FIGS. 18 and 19 are plots showing performance results based on the simulation study.

A single simulation trial involved choosing 50 random image samples from the set of 8767 and analyzing each over ten trigger events, where each event was an advancement of a single defect category's classifier family. We computed the "best" ten triggers for each sample using the method described here with a "one step ahead" greedy optimization and all misclassification errors assigned unit cost. This was compared to a random trigger selection for each sample, where the ten trigger events were selected at random from the set of all possible triggers. To assess average performance, 1000 simulation trials were performed. FIG. 18 is a histogram that illustrates the difference between the baseline random (A) and greedy optimal (B). These histograms are aggregated over the 1000 trials and 50 image samples at each trial.

Figure 19:
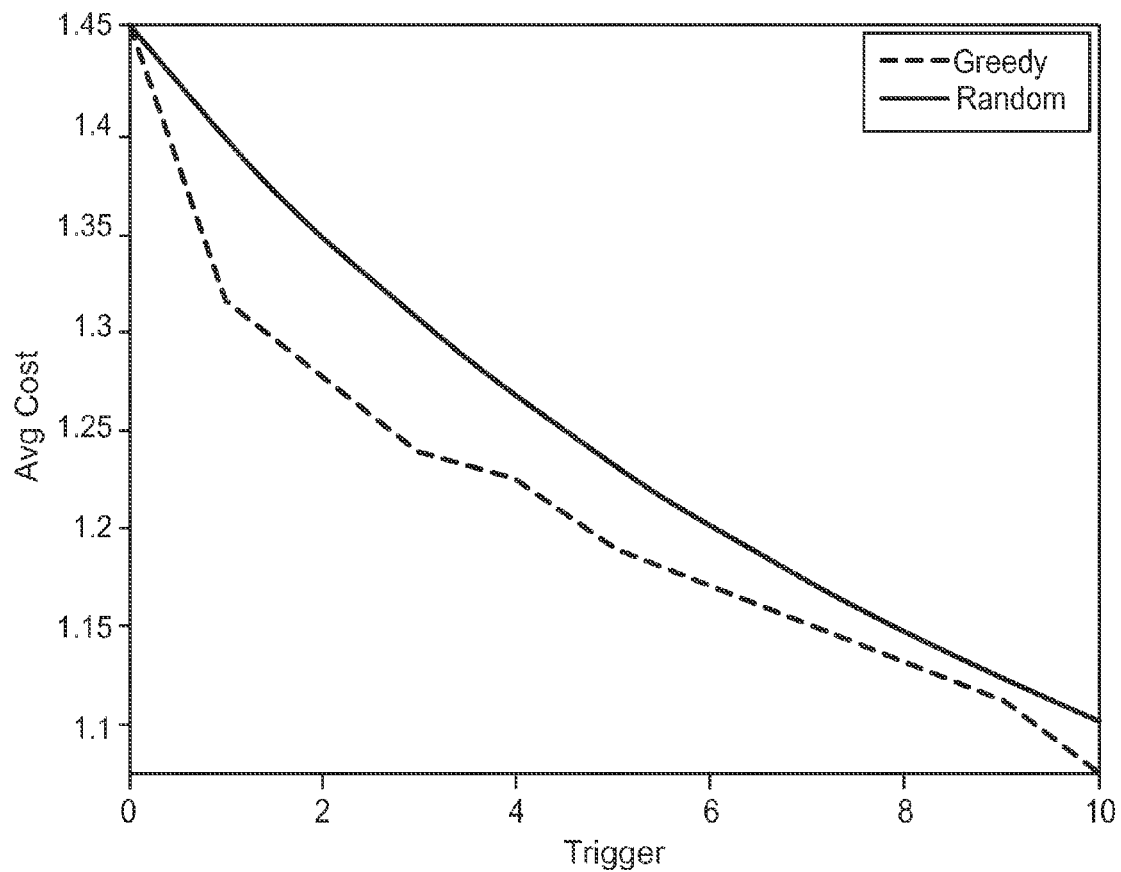
Figure 20:
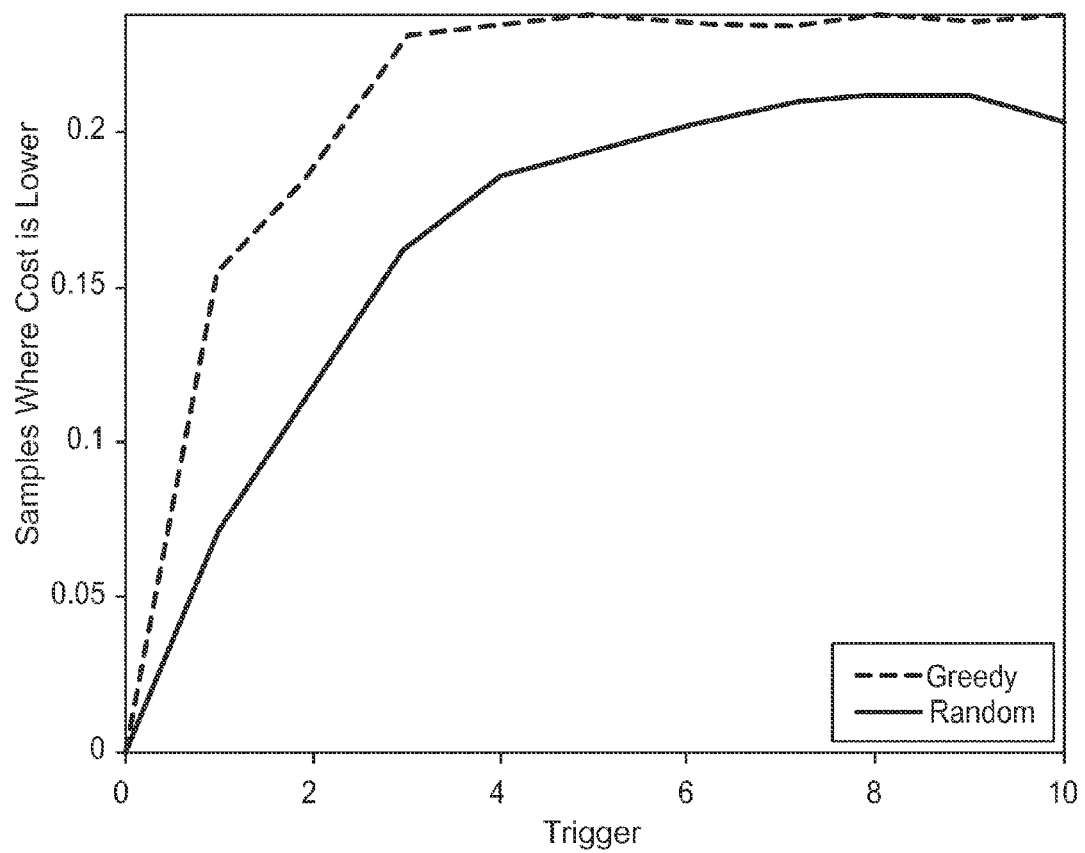
FIG. 20 is a comparative plot that shows the average (across trials) fraction of samples in which a particular triggering strategy yielded a lower cost.

FIGS. 19 and 20 are plots showing performance results based on the simulation study. FIG. 19 illustrates the average mis-classification cost across trials/images. As described above, all mis-classifications were assigned a unit cost. As shown, the greedy optimal controlled trigger has lower average cost across all events than a random trigger with the most substantial difference observed after the first couple of triggers. FIG. 20 is a comparative plot that shows the average (across trials) fraction of the 50 samples in which a particular triggering strategy yielded a lower cost. As shown, the greedy trigger gave better performance on average for a larger proportion of the 50 samples.

The controlled Markov chain model for feature triggering is demonstrated to give a clear improvement. Further improvement may be gained by using more sophisticated control optimization since the greedy algorithm may be considered a simple yet efficient scheme. Also, the set of features considered in the study is relatively small (26 features). The techniques may be even more advantageous when it is necessary to choose from a larger feature set. In such cases, dynamically discovering the best features to compute may have even more advantage in a live production line. There is minimal online computation associated with this technique since, in one embodiment, it can be implemented through a table lookup and the expensive construction of the lookup table can be done offline.

An alternative case of triggering is when images are compared to recent past frames to control for continuation of the current quality, and a change is detected, triggering more detailed analysis. For example, if the current web is in the stage of "good web," often simple features such as variance can be used to detect the appearance of a new non-uniformity. This detection triggers more detailed analysis, which then calls for the computation of additional features. For example, recent past sample images obtained from a material in an online product line can be charted following the procedure described therein. This can be done with previously labeled training data, a set that can be augmented with the recently charted frames. Once a significant change in charting value is discovered, triggering occurs, calling for an augmented set of features to detect the class and severity of any non-uniformity within the new frame.

In some embodiments, computer hardware may be selected to complement the dynamic feature triggering algorithm to further reduce feature extraction time in an online environment. As mentioned previously, feature extraction usually involves some standard image processing routines. Such operations for online feature extraction for uniformity processing can be performed more quickly on graphics processing units (GPUs) than standard CPUs.

GPUs were traditionally designed with graphics pipeline for rendering 3D scenes on a computer display. Specific processing components along the pipeline are often referred to as shaders. A set of geometric primitives (typically triangular) are first processed by vertex shaders to create the underlying shape of the figure in the GPUs coordinate system. Then lighting may be applied by pixel shaders, and camera projection via geometric shaders. Rasterization and texturing are next. Finally, the visible scenes are selected and the image is rendered.

Several major steps in the pipeline amount to matrix-vector operations, which turn out to be exactly the operations required to apply certain types of feature extraction manipulations, e.g., Gabor-type filters, to an image captured from a web material. GPUs are highly optimized to perform these computations and exploit parallelism by using multiple processors to analyze different pixel regions simultaneously. All steps in the standard pipeline of a GPU may not be required and, as such, certain specialized shaders may be under-utilized. Fortunately, modern GPUs make use of unified shaders that can perform any processing step. Also, a more granular API is being exposed by modern GPUs, thus broadening the scope of potential applications for GPU processing. One example is the CUDA (Compute Unified Device Architecture) API extension to the C programming language recently released by NVidia Corporation. Enhancements accompanying this architecture, such as an exposed shared memory region and faster communication with the driver CPU, aim to make the GPU suitable for general purpose high performance computing.

For many applications of uniformity processing, a large bank of Gabor filters will be used to extract features using frequency domain filtering. Substantial performance gains may be achieved when implementing spatial and frequency domain filtering on GPUs as compared to a traditional CPU implementation. For large sets of features, it is often more efficient to perform the filtering in frequency domain. This is due to the fact that the FFT of the target image need only be computed once; it can then be processed in parallel by multiple filters.

In some examples, uniformity processing uses Gabor filters having sinusoidal components directions that are aligned with one of the principle axes, and a Gaussian window which provides localization. This arises naturally from expected defects (such as chatter) that are similarly oriented. Such filters are separable, meaning they can be formed from an outer product of two one-dimensional filters. Spatial convolution can be sped up in this case by decomposing the full two-dimensional convolution into separate 1-D convolutions. This can be exploited when processing smaller filters to achieve the best performance.

Aspects of GPUs, including parallel pixel computations and optimized matrix-vector operations, make them useful hardware components for feature extraction in rapid uniformity processing. Another method for accelerating the data processing is through implementation in hardware using ASICs (application-specific integrated circuits) or FPGAs (field-programmable gate arrays).

Various embodiments of the invention have been described. These and other embodiments are within the scope of the following claims.

The invention claimed is:

1. A method comprising:
executing rating software on a computer to automatically assign a discrete rating label for a non-uniform pattern to each of a plurality of training images and compute a classification model based on the rating labels assigned to the training samples, wherein the rating software receives input from a user for only a subset of the training images and computes the rating labels for all of the remaining training images based upon the input;
processing in real-time a sample image captured from a manufactured web material with hardware components of a pipelined graphical processing unit (GPU) integrated within a computerized inspection system to extract a first plurality of features from the image in parallel; and
computing a severity level for the non-uniformity pattern for the sample image of the web material with the computerized inspection system from the first plurality of features in accordance with the classification model.

2. The method of claim 1, wherein automatically assigning the discrete rating labels comprises:
computing, with the rating software, a plurality of image clusters for a representative subset of the training images;
receiving individual rating labels assigned to the image clusters by the user;
automatically propagating the individual rating labels assigned to the image clusters by a user to all of the training images within the respective image clusters; and
automatically computing rating labels and assigning the computed rating labels to all remaining ones of the training images not included within the representative subset of the training images for each of the classes of patterns.

3. The method of claim 1, further comprising:
processing the first plurality of features with the inspection system with a decision-making model that defines a chain of triggers to dynamically select a second plurality of features to extract from the image in accordance with the model;
determining, in accordance with the decision-making model, an expected reduction in cost of misclassifying the sample image with respect to the non-uniformity pattern if the second plurality of features are extracted from the sample image;
when the expected reduction in cost exceeds a threshold, processing the sample image with the hardware components of the pipelined GPU of the inspection system to extract the second set of features; and
computing the severity level for the non-uniformity pattern for the web material with the inspection system using the first plurality of features and the second plurality of features extracted from the image.

4. The method of claim 1, wherein automatically assigning rating labels comprises, for each of the unlabeled training images not included within the representative subset of the training images:
- computing a pair-wise distance for the numerical descriptor of the unlabeled training image to the numerical descriptor of each of the labeled images within the representative subset of the training images;
- computing a set of probabilities for each specified class of patterns, wherein the set of probabilities for each class of patterns includes a probability for each of the rating labels specified for the class of pattern and indicates the probability that the unlabeled training image is a member of the training images that have been assigned that particular rating label for that particular class of pattern; and
- assigning to the unlabeled training image the rating labels having the highest probability within each of the classes of patterns.

5. The method of claim 1, further comprising:
- computing, with the rating software, a continuous ranking of the training images based on the discrete rating labels assigned to the training images; and
- computing, with the computerized inspection system, the severity level of the non-uniform pattern for the web based on the continuous ranking of the training image.

6. A method for inspecting web material in real-time and computing a severity of a non-uniformity pattern as the web material is manufactured, the method comprising:
- receiving, with an online computerized inspection system, an image captured from a web material being manufactured;
- processing the image with the inspection system to extract a first set of features;
- processing the first set of features with the inspection system with a decision-making model that defines a chain of triggers to dynamically select a second set of features to extract from the image in accordance with the model;
- determining, in accordance with the model, an expected reduction in cost of misclassifying the image with respect to the non-uniformity pattern if the second set of features are extracted from the image;
- when the expected reduction in cost exceeds a threshold, invoking hardware components of a pipelined graphical processing unit (GPU) integrated within the inspection system to process the image with the inspection system to extract the second set of features; and
- computing the severity level for the non-uniformity pattern for the web material with the inspection system using the first set of features and the second set of features extracted from the image.

7. The method of claim 6, wherein the model comprises a Markov model that defines a chain of one or more dynamic triggers for controlling the selection of the second set of features to extract and any additional sets of features to extract from the image.

8. The method of claim 6, further comprising presenting a user interface to output the severity level to a user.

9. The method of claim 8, wherein presenting a user interface comprises updating a chart to graph the severity level of the non-uniform pattern for the web material over time.

10. The method of claim 8, further comprising:
- receiving input from the user; and
- adjusting one or more process control parameters for the manufactured web material in response to the input.

11. An online computerized inspection system for inspecting web material in real-time and computing a severity of a non-uniformity pattern as the web material is manufactured, the inspection system comprising:
- a memory to store a decision-making model that defines a chain of dynamic triggers for selecting in real-time which features to extract from an image; and
- a computer executing software to process a sample image captured from a manufactured web material currently being manufactured to extract a first set of features,
- wherein the software applies the decision-making model to repeated dynamically trigger selection of additional sets of features and to extract from the sample image and invoke hardware components of a pipelined graphical processing unit (GPU) of the inspection system to extract the additional sets of features until the extracted features are sufficient to compute a severity level of a non-uniformity pattern for the web material within a defined level of confidence.

12. The inspection system of claim 11,
- wherein the software applies the model to trigger selection of a second set of features to extract from the new image,
- wherein, when triggered, the software dynamically selects the second set of features from an overall set of features based on the first set of features extracted from the image, and
- wherein the software processes the sample image to extract the second set of features from the image and compute the severity level of the non-uniformity pattern based on the first set of features and the second set of features.

13. The inspection system of claim 12, wherein the model comprises a Markov model.

14. An online computerized inspection system for inspecting web material in real-time comprising:
- a memory to store a model that represents a continuous ranking of the training images as a plurality of points within a multidimensional feature space, wherein each of the points within the multidimensional space corresponds to a feature vector for a different one of the training images; and
- a pipelined graphical processing unit (GPU) of the inspection system to process a sample image captured from a manufactured web material to extract a plurality of features in parallel from the sample image using parallel hardware components of the GPU,
- wherein the computerized inspection system computes a severity level of a non-uniform pattern from the extracted features for the sample image of the web material on a continuous scale based on the model of the training images.

15. A system comprising:
- rating software executing on a processor, wherein the rating software extracts features from each of a plurality of training images by computing a numerical descriptor for each of the training images from pixel values of the respective training image, wherein the rating software performs a first clustering process to process the numerical descriptors of the training images to automatically select a representative subset of the training images and compute a plurality of image clusters for the representative subset of training images; and
- a user interface presented by the rating software having input mechanisms to receive input from a user specifying one or more classes of patterns present within the representative training images and a set of rating labels for each of the classes of patterns, wherein the user interface further includes input mechanisms to receive input assigning an individual rating label to each of the image clusters for each of the specified classes of patterns, wherein, for each of the image clusters, the rating software automatically propagates each of the individual rating labels assigned to the classes of patterns for the image cluster to all of the training images within that image cluster;

training software to compute a classification model based on the rating labels assigned to the training samples; and an online computerized inspection system comprising a pipelined graphical processing unit (GPU) of the inspection system to process a new image captured from a manufactured web material to extract a plurality of features in parallel from the new image and compute a severity level of a non-uniform pattern for the web material continuous scale based on the classification model.

16. A method of training a user comprising:

executing rating software on a computer to automatically assign a discrete rating label for a non-uniform pattern to each of a plurality of training images and compute a classification model based on the rating labels assigned to the training samples by one or more experts;

processing in real-time a sample image captured from a manufactured web material with a computerized inspection system to extract a first plurality of features from the image;

computing a severity level for the non-uniformity pattern for the sample image of the web material with the computerized inspection system from the first plurality of features in accordance with the classification model; and displaying both the sample image and the severity level computed from the classification model to a user as training information for visualizing the non-uniformity pattern in the same manner as the experts.

17. The method of claim 16, receiving input from the user requesting an increase or decrease in the severity level for the non-uniformity pattern; and adjusting one or more process control parameters for the manufactured web material in response to the input.

18. The method of claim 16, wherein the rating software receives input from a user for only a subset of the training images and computes the rating labels for all of the remaining training images based upon the input.

* * * * *